US009050125B2

(12) United States Patent
Boudreaux et al.

(10) Patent No.: US 9,050,125 B2
(45) Date of Patent: Jun. 9, 2015

(54) ULTRASONIC SURGICAL INSTRUMENT WITH MODULAR END EFFECTOR

(75) Inventors: Chad P. Boudreaux, Cincinnati, OH (US); Kevin L. Houser, Springboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 744 days.

(21) Appl. No.: 13/269,899

(22) Filed: Oct. 10, 2011

(65) Prior Publication Data
US 2013/0090577 A1  Apr. 11, 2013

(51) Int. Cl.
*A61B 17/32* (2006.01)
*A61B 17/00* (2006.01)
*A61B 17/29* (2006.01)

(52) U.S. Cl.
CPC . *A61B 17/320092* (2013.01); *A61B 2017/0046* (2013.01); *A61B 2017/00477* (2013.01); *A61B 2017/2929* (2013.01)

(58) Field of Classification Search
CPC .............. A61B 17/320092; A61B 2017/0046; A61B 2017/00477; A61B 2017/2929; A61B 2017/2903; A61B 2017/2912
USPC ........................ 606/1, 169, 205; 600/439, 471
See application file for complete search history.

(56) References Cited

U.S. PATENT DOCUMENTS

| 4,878,493 | A | 11/1989 | Pasternak et al. |
| 5,107,155 | A | 4/1992 | Yamaguchi |
| 5,277,694 | A | 1/1994 | Leysieffer et al. |
| 5,322,055 | A | 6/1994 | Davison |
| 5,449,370 | A | 9/1995 | Vaitekumas |
| 5,630,420 | A | 5/1997 | Vaitekunas |
| 5,800,336 | A | 9/1998 | Ball et al. |
| 5,873,873 | A | 2/1999 | Smith et al. |
| 5,893,835 | A * | 4/1999 | Witt et al. ..................... 606/205 |

(Continued)

FOREIGN PATENT DOCUMENTS

| WO | WO 2009/046394 | 4/2009 |
| WO | WO 2009/070780 | 6/2009 |
| WO | WO 2009/073608 | 6/2009 |

OTHER PUBLICATIONS

European Search Report dated Oct. 24, 2013 for Application No. EP 12188042.

(Continued)

*Primary Examiner* — Julian W Woo
(74) *Attorney, Agent, or Firm* — Frost Brown Todd LLC

(57) ABSTRACT

A surgical instrument having a transmission assembly, a transducer, and a handle assembly is configured for coupling the transmission assembly to the handle assembly using a locking mechanism. The locking mechanism is operable to restrict the rotational movement of an actuator coupling member and the transducer relative to the handle assembly. The locking mechanism may also be operable to lock a trigger of the handle assembly in a first position. An inner tubular actuating member of the transmission assembly may be threadably attachable to the actuator coupling member or the actuator coupling member may include a latching mechanism to couple to a flared portion of the inner tubular actuating member. A waveguide of the transmission assembly may also be threadably attachable to the transducer. In one alternative, the trigger may be configured to operate the locking mechanism, either in the first position or when pivoted distally to a third position.

17 Claims, 15 Drawing Sheets

(56) References Cited

U.S. PATENT DOCUMENTS

| | | | |
|---|---|---|---|
| 5,935,144 | A | 8/1999 | Estabrook |
| 5,938,633 | A | 8/1999 | Beupre |
| 5,944,737 | A | 8/1999 | Tsonton et al. |
| 5,980,510 | A | 11/1999 | Tsonton et al. |
| 6,051,010 | A | 4/2000 | Dimatteo et al. |
| 6,325,811 | B1 | 12/2001 | Messerly |
| 6,500,176 | B1 | 12/2002 | Truckai et al. |
| 6,514,267 | B2 | 2/2003 | Jewett |
| 6,520,185 | B1 | 2/2003 | Bommannan et al. |
| 6,561,983 | B2 | 5/2003 | Cronin et al. |
| 6,626,901 | B1 | 9/2003 | Treat et al. |
| 6,666,875 | B1 | 12/2003 | Sakurai et al. |
| 6,783,524 | B2 | 8/2004 | Anderson et al. |
| 6,982,696 | B1 | 1/2006 | Shahoian |
| 7,112,201 | B2 | 9/2006 | Truckai et al. |
| 7,125,409 | B2 | 10/2006 | Truckai et al. |
| 7,169,146 | B2 | 1/2007 | Truckai et al. |
| 7,186,253 | B2 | 3/2007 | Truckai et al. |
| 7,189,233 | B2 | 3/2007 | Truckai et al. |
| 7,220,951 | B2 | 5/2007 | Truckai et al. |
| 7,292,227 | B2 | 11/2007 | Fukumoto et al. |
| 7,309,849 | B2 | 12/2007 | Truckai et al. |
| 7,311,709 | B2 | 12/2007 | Truckai et al. |
| 7,354,440 | B2 | 4/2008 | Truckal et al. |
| 7,381,209 | B2 | 6/2008 | Truckai et al. |
| 7,416,101 | B2 | 8/2008 | Shelton, IV et al. |
| 7,464,846 | B2 | 12/2008 | Shelton, IV et al. |
| D594,983 | S | 6/2009 | Price et al. |
| 7,583,564 | B2 | 9/2009 | Ketahara et al. |
| 7,638,958 | B2 | 12/2009 | Philipp et al. |
| 7,738,971 | B2 | 6/2010 | Swayze et al. |
| 7,846,155 | B2 | 12/2010 | Houser et al. |
| 7,959,050 | B2 | 6/2011 | Smith et al. |
| 8,142,461 | B2 | 3/2012 | Houser et al. |
| 8,419,758 | B2 * | 4/2013 | Smith et al. ............... 606/169 |
| 2006/0079874 | A1 | 4/2006 | Faller et al. |
| 2007/0191713 | A1 | 8/2007 | Eichmann et al. |
| 2007/0282333 | A1 | 12/2007 | Fortson et al. |
| 2008/0057470 | A1 | 3/2008 | Levy et al. |
| 2008/0200940 | A1 | 8/2008 | Eichmann et al. |
| 2008/0221491 | A1 | 9/2008 | Slayton et al. |
| 2008/0228104 | A1 | 9/2008 | Uber, III et al. |
| 2008/0255413 | A1 | 10/2008 | Zemlok et al. |
| 2009/0043797 | A1 | 2/2009 | Dorie et al. |
| 2009/0138006 | A1 | 5/2009 | Bales et al. |
| 2009/0143797 | A1 | 6/2009 | Smith et al. |
| 2009/0143798 | A1 | 6/2009 | Smith et al. |
| 2009/0143799 | A1 | 6/2009 | Smith et al. |
| 2009/0143800 | A1 | 6/2009 | Deville et al. |
| 2009/0143801 | A1 | 6/2009 | Deville et al. |
| 2009/0143802 | A1 | 6/2009 | Deville et al. |
| 2009/0143803 | A1 | 6/2009 | Palmer et al. |
| 2009/0143804 | A1 | 6/2009 | Palmer et al. |
| 2009/0143805 | A1 | 6/2009 | Palmer et al. |
| 2009/0209979 | A1 | 8/2009 | Yates et al. |
| 2009/0209990 | A1 | 8/2009 | Yates et al. |
| 2010/0069940 | A1 | 3/2010 | Miller et al. |
| 2010/0331742 | A1 | 12/2010 | Masuda |
| 2011/0015660 | A1 | 1/2011 | Wiener et al. |
| 2011/0087212 | A1 | 4/2011 | Aldridge et al. |
| 2011/0087218 | A1 | 4/2011 | Boudreaux et al. |
| 2011/0152901 | A1 | 6/2011 | Woodruff et al. |

OTHER PUBLICATIONS

U.S. Appl. No. 13/151,471, filed Jun. 2, 2011, Stulen.
U.S. Appl. No. 13/151,481, filed Jun. 2, 2011, Yates et al.
U.S. Appl. No. 13/151,488, filed Jun. 2, 2011, Shelton IV et al.
U.S. Appl. No. 13/151,498, filed Jun. 2, 2011, Felder et al.
U.S. Appl. No. 13/151,503, filed Jun. 2, 2011, Madan et al.
U.S. Appl. No. 13/151,509, filed Jun. 2, 2011, Smith et al.
U.S. Appl. No. 13/151,512, filed Jun. 2, 2011, Houser et al.
U.S. Appl. No. 13/151,515, filed Jun. 2, 2011, Felder et al.
U.S. Appl. No. 13/176,875, filed Jul. 6, 2011, Smith et al.
U.S. Appl. No. 13/269,870, filed Oct. 10, 2011, Houser et al.
U.S. Appl. No. 13/269,883, filed Oct. 10, 2011, Mumaw et al.
U.S. Appl. No. 13/269,899, filed Oct. 10, 2011, Boudreaux et al.
U.S. Appl. No. 13/270,667, filed Oct. 11, 2011, Timm et al.
U.S. Appl. No. 13/270,684, filed Oct. 11, 2011, Madan et al.
U.S. Appl. No. 13/270,701, filed Oct. 11, 2011, Johnson et al.
U.S. Appl. No. 13/271,352, filed Oct. 12, 2011, Houser et al.
U.S. Appl. No. 13/271,364, filed Oct. 12, 2011, Houser et al.
U.S. Appl. No. 13/274,480, filed Oct. 17, 2011, Mumaw et al.
U.S. Appl. No. 13/274,496, filed Oct. 17, 2011, Houser et al.
U.S. Appl. No. 13/274,507, filed Oct. 17, 2011, Houser et al.
U.S. Appl. No. 13/274,516, filed Oct. 17, 2011, Haberstich et al.
U.S. Appl. No. 13/274,540, filed Oct. 17, 2011, Madan.
U.S. Appl. No. 13/274,805, filed Oct. 17, 2011, Price et al.
U.S. Appl. No. 13/274,830, filed Oct. 17, 2011, Houser et al.
U.S. Appl. No. 13/275,495, filed Oct. 18, 2011, Houser et al.
U.S. Appl. No. 13/275,514, filed Oct. 18, 2011, Houser et al.
U.S. Appl. No. 13/275,547, filed Oct. 18, 2011, Houser et al.
U.S. Appl. No. 13/275,563, filed Oct. 18, 2011, Houser et al.
U.S. Appl. No. 13/276,660, filed Oct. 19, 2011, Houser et al.
U.S. Appl. No. 13/276,673, filed Oct. 19, 2011, Kimball et al.
U.S. Appl. No. 13/276,687, filed Oct. 19, 2011, Price et al.
U.S. Appl. No. 13/276,707, filed Oct. 19, 2011, Houser et al.
U.S. Appl. No. 13/276,725, filed Oct. 19, 2011, Houser et al.
U.S. Appl. No. 13/276,745, filed Oct. 19, 2011, Stulen et al.
U.S. Appl. No. 13/277,328, filed Oct. 20, 2011, Houser et al.
Dietz, T. et al., Partially Implantable Vibrating Ossicular Prosthesis, Transducers'97, vol. 1, International Conference on Solid State Sensors and Actuators, (Jun. 16-19, 1997) pp. 433-436 (Abstract).
"System 6 Aseptic Battery System," Stryker (2006) pp. 1-2.

\* cited by examiner

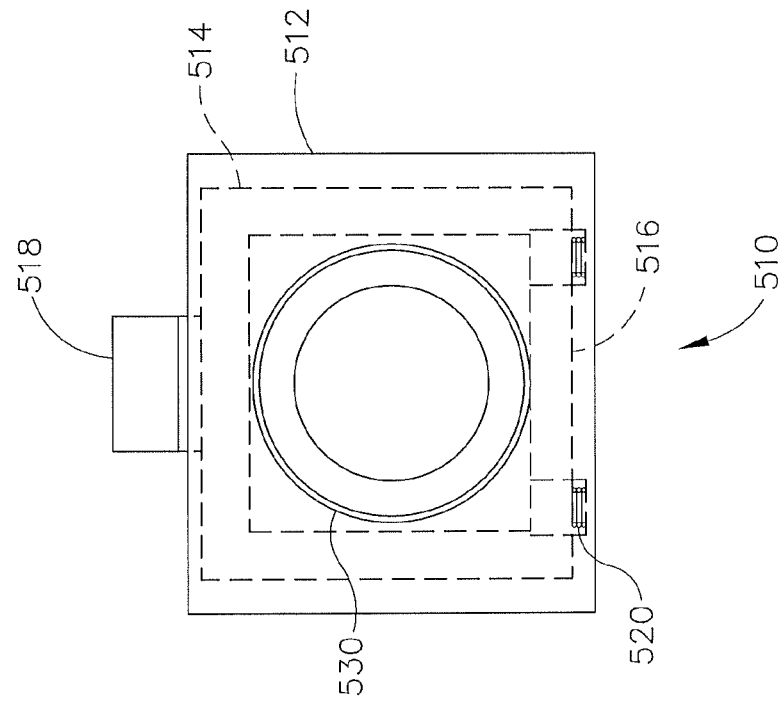
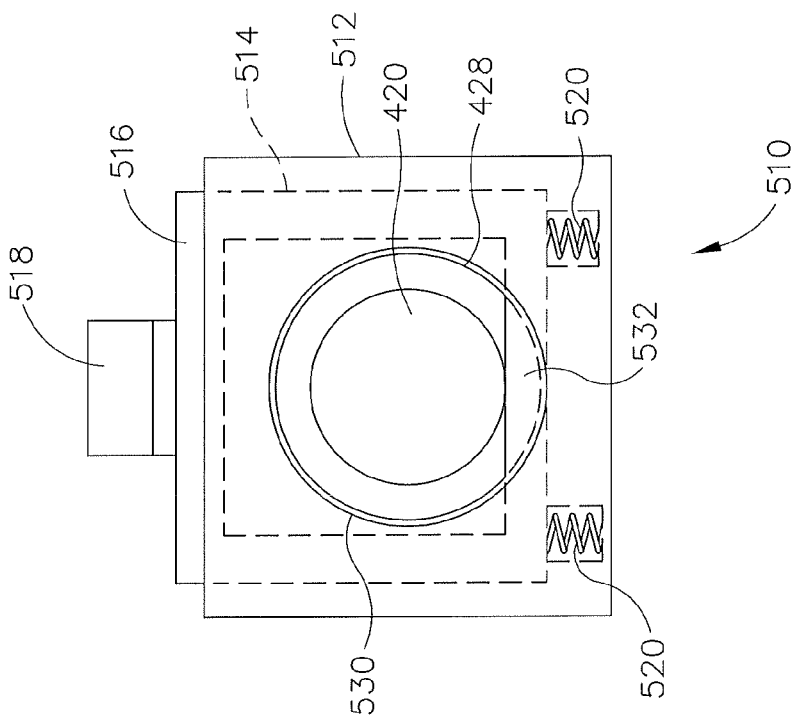

ULTRASONIC SURGICAL INSTRUMENT WITH MODULAR END EFFECTOR

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. Pub. No. 2006/0079874, entitled "Tissue Pad for Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pat. Pub. No. 2011/0015660, entitled "Rotating Transducer Mount for Ultrasonic Surgical Instruments," published Jan. 20, 2011 (now U.S. Pat. No. 8,461,744), the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; and U.S. Pat. Pub. No. 2011/0087218, entitled "Surgical Instrument Comprising First and Second Drive Systems Actuatable by a Common Trigger Mechanism," published Apr. 14, 2011 (now U.S. Pat. No. 8,939,974), the disclosure of which is incorporated by reference herein. Additionally, such surgical tools may include a cordless transducer such as that disclosed in U.S. Pat. Pub. No. 2009/0143797, entitled "Cordless Handheld Ultrasonic Cautery Cutting Device," published Jun. 4, 2009 (now U.S. Pat. No. 8,419,757), the disclosure of which is incorporated by reference herein. In addition, the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

While several systems and methods have been made and used for surgical instruments, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 9A depicts a rear elevation view of an exemplary latching member in a latched position showing an inner tubular actuating member inserted therein;

FIG. 9B depicts a rear elevation view of the latching member of FIG. 9A in an unlatched position;

Figure 1:
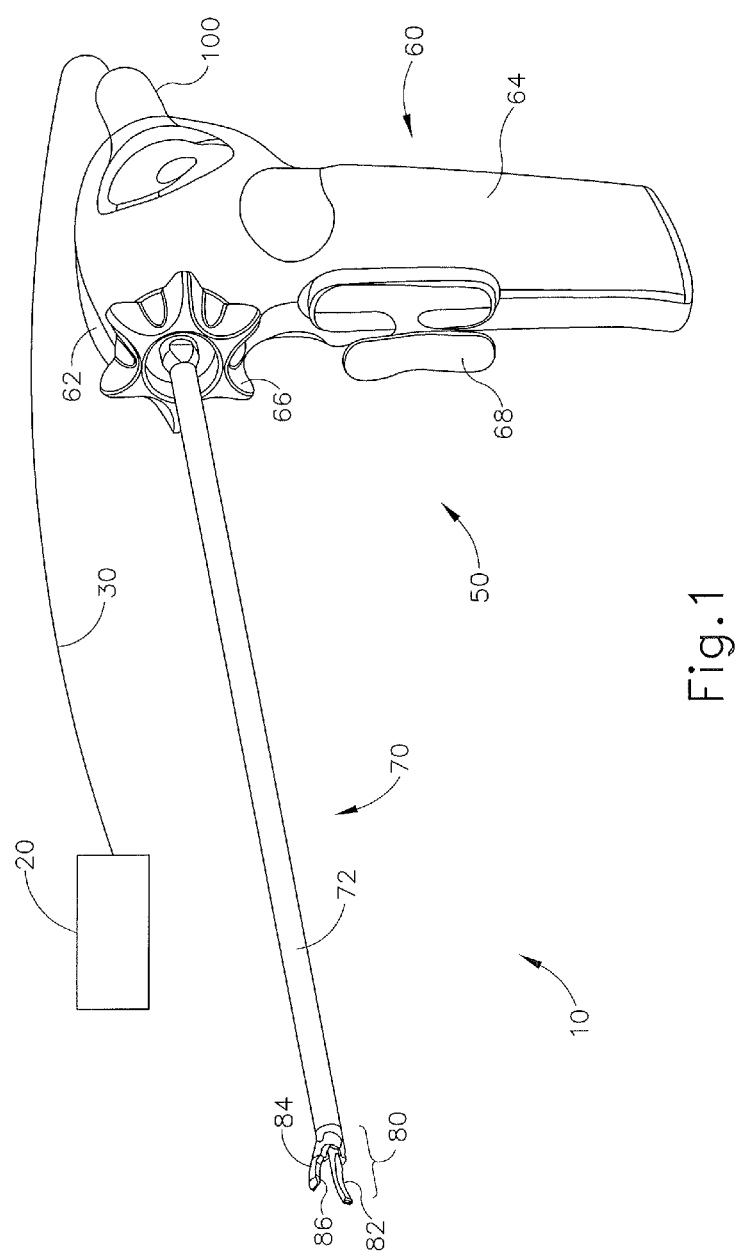
FIG. 1 depicts a perspective view of an exemplary surgical system having a surgical instrument and a generator.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Ultrasonic Surgical System

FIG. 1 shows an exemplary ultrasonic surgical system (10) comprising an ultrasonic surgical instrument (50), a generator (20), and a cable (30) coupling generator (20) to surgical instrument (50). In some versions, generator (20) comprises a GEN 300 sold by Ethicon Endo-Surgery, Inc. of Cincinnati, Ohio. It should also be understood that generator (20) may be constructed in accordance with the teachings of U.S. Pub. No. 2011/0087212, entitled "Surgical Generator for Ultrasonic and Electrosurgical Devices," published Apr. 14, 2011 (now U.S. Pat. No. 8,986,302), the disclosure of which is incorporated by reference herein. While surgical instrument (50) is described herein as an ultrasonic surgical instrument, it should be understood that the teachings herein may be readily applied to a variety of surgical instruments, including but not limited to endocutters, graspers, cutters, staplers, clip appliers, access devices, drug/gene therapy delivery devices, and energy delivery devices using ultrasound, RF, laser, etc., and/or any combination thereof as will be apparent to one of ordinary skill in the art in view of the teachings herein. Moreover, while the present example will be described in reference to a cable-connected surgical instrument (50), it should be understood that surgical instrument (50) may be adapted for cordless operation, such as that disclosed in U.S. Pat. Pub. No. 2009/0143797, entitled "Cordless Hand-held Ultrasonic Cautery Cutting Device," published Jun. 4, 2009 (now U.S. Pat. No. 8,419,757), the disclosure of which is incorporated by reference herein. For instance, surgical device (50) may include an integral and portable power source such as a battery, etc. Furthermore, surgical device (50) may also be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

Surgical instrument (50) of the present example includes a multi-piece handle assembly (60), an elongated transmission assembly (70), and a transducer (100). Transmission assembly (70) is coupled to multi-piece handle assembly (60) at a proximal end of transmission assembly (70) and extends distally from multi-piece handle assembly (60). In the present example, transmission assembly (70) is configured as an elongated, thin tubular assembly for endoscopic use, but it should be understood that transmission assembly (70) may alternatively be a short assembly, such as those disclosed in U.S. Pat. Pub. No. 2007/0282333, entitled "Ultrasonic Waveguide and Blade," published Dec. 6, 2007, and U.S. Pat. Pub. No. 2008/0200940, entitled "Ultrasonic Device for Cutting and Coagulating," published Aug. 21, 2008, the disclosures of which are incorporated by reference herein. Transmission assembly (70) of the present example comprises an outer sheath (72), an inner tubular actuating member (not shown), a waveguide (not shown), and an end effector (80) located on the distal end of transmission assembly (70). In the present example, end effector (80) comprises a blade (82) that is mechanically and acoustically coupled to the waveguide, a clamp arm (84) operable to pivot at the proximal end of transmission assembly (70), and a clamp pad (86) coupled to clamp arm (84). Exemplary versions of end effector (80) and transmission assembly (70) will be discussed in greater detail below in reference to the example shown in FIG. 4. In some versions, transducer (100) comprises a plurality of piezoelectric elements (not shown) that are compressed between first resonator (not shown) and second resonator (not shown) to form a stack of piezoelectric elements. The piezoelectric elements may be fabricated from any suitable material, for example, lead zirconate-titanate, lead meta-niobate, lead titanate, and/or any suitable piezoelectric crystal material, for example. Transducer (100) further comprises electrodes, including at least one positive electrode and at least one negative electrode that are configured to create a voltage potential across the one or more piezoelectric elements, such that the piezoelectric elements convert the electrical power into ultrasonic vibrations. The ultrasonic vibrations are transmitted to blade (82) via the waveguide in transmission assembly (70).

Multi-piece handle assembly (60) of the present example comprises a mating housing portion (62) and a lower portion (64). Mating housing portion (62) is configured to receive transducer (100) at a proximal end of mating housing portion (62) and to receive the proximal end of transmission assembly (70) at a distal end of mating housing portion (62). A rotation knob (66) is shown in the present example to rotate transmission assembly (70) and transducer (100), but it should be understood that rotation knob (66) is merely optional. Mating housing portion (62) will be discussed in greater detail below in reference to FIG. 2. Lower portion (64) of multi-piece handle assembly (60) shown in FIG. 1 includes a trigger (68) and is configured to be grasped by a user using a single hand. One merely exemplary alternative version for lower portion (64) is depicted in FIG. 1 of U.S. Pat. Pub. No. 2011/0015660, entitled "Rotating Transducer Mount for Ultrasonic Surgical Instruments," published Jan. 20, 2011 (now U.S. Pat. No. 8,461,744), the disclosure of which is incorporated by reference herein. Toggle buttons (69), shown in FIG. 2 of the present disclosure, are located on a distal surface of lower portion (64) and are operable to selectively activate transducer (100) at different operational levels using generator (20). For instance, a first toggle button (69) may activate transducer (100) at a maximum energy level while a second toggle button (69) may activate transducer (100) at a minimum, non-zero energy level. Of course, toggle buttons (69) may be configured for energy levels other than a maximum and/or minimum energy level as will be apparent to one of ordinary skill in the art in view of the teachings herein. Of course, a single toggle button (69) may be used or, in some versions, more than two toggle buttons (69) may be used. While multi-piece handle assembly (60) has been described in reference to two distinct portions (62, 64), it should be understood that multi-piece handle assembly (60) may be a unitary assembly with both portions (62, 64) combined. Multi-piece handle assembly (60) may alternatively be divided into multiple discrete components, such as a separate trigger portion (operable either by a user's hand or foot) and a separate mating housing portion (62). Such a trigger portion may be operable to activate transducer (100) and may be remote from mating housing portion (62). Multi-piece handle assembly (60) may be constructed from a durable plastic (such as polycarbonate or a liquid crystal polymer), ceramics, metals, and/or any other suitable material as will be apparent to one of ordinary skill in the art in view of the teachings herein. Other configurations for multi-piece handle assembly (60) will also be apparent to those of ordinary skill in the art in view of the teachings herein. For instance, in some versions trigger (68) may be omitted and surgical instrument (50) may be activated by a controlled of a robotic system. In other versions, surgical instrument (50) may be activated when coupled to generator (20). Further still, surgical instrument (50) may be constructed in accordance with at least some of the teachings of U.S. Pat. Pub. No. 2006/0079874; U.S. Pat. Pub. No. 2007/0191713; U.S. Pat. Pub. No. 2007/0282333; U.S. Pat. Pub. No. 2008/0200940; U.S. Pat. Pub. No. 2011/0015660 (now U.S. Pat. No. 8,461,744); U.S. Pat. No. 6,500,176; U.S. Pat. Pub. No. 2011/0087218 (now U.S. Pat. No. 8,939,974); and/or U.S. Pat. Pub. No. 2009/0143797 (now U.S. Pat. No. 8,419,757).

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

II. Exemplary Coupling Assemblies for Ultrasonic Surgical Instrument

In some instances it may be useful to detach transmission assembly (70) from multi-piece handle assembly (60) and transducer (100). For instance, a detachable transmission assembly (70) may permit the reuse of multi-piece handle assembly (60) with multiple transmission assemblies (70) having various end effectors (80). By way of example only, the various end effectors (80) may have different sized and/or shaped blades (82) or the various end effectors (80) may have entirely different functions, such as RF end effectors, stapling end effectors, cutting end effectors, etc. Further still, transmission assemblies (70) may have various shaft lengths as well. Furthermore, a single multi-piece handle assembly (60) may be reused for different operations by a user by removing a dirty transmission assembly (70), optionally cleaning multi-piece handle assembly (60), and coupling a new transmission assembly (70) to multi-piece handle assembly (60) for a new operation. Accordingly, configuring multi-piece handle assembly (60) to couple with a variety of transmission assemblies (70) may be preferable for some users of surgical instrument (50).

A. Exemplary Multi-Piece Handle Assembly

Figure 2:
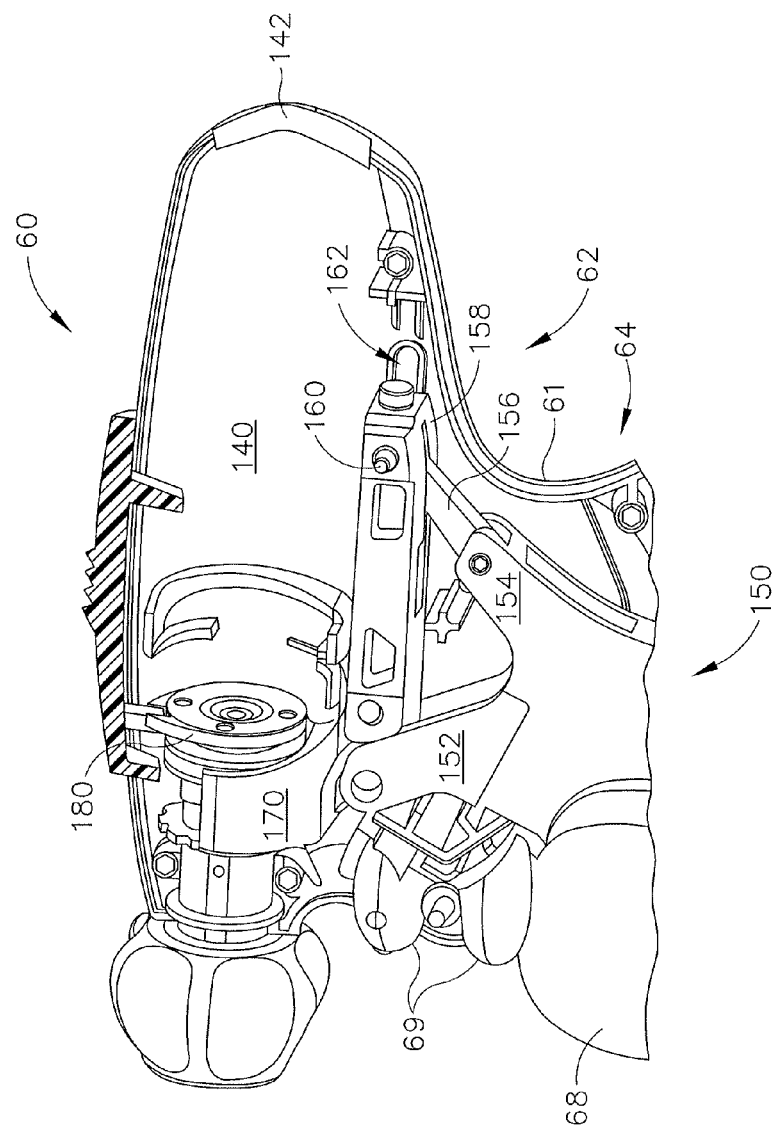
FIG. 2 depicts a partial side elevation view of an exemplary surgical instrument with a portion of a cover removed to show the interior of a mating housing portion of an exemplary multi-piece handle assembly.

FIG. 2 shows a partial side view of multi-piece handle assembly (60) with a portion of a cover (61) removed to show the internal components contained within mating housing portion (62) and a section of lower portion (64). As described above, lower portion (64) includes a pivotable trigger (68) and a pair of toggle buttons (69). Trigger (68) of the present example is pivotable from a distal, open position to a proximal, closed position. A trigger assembly (150) is coupled to trigger (68) and is pivotally supported within multi-piece handle assembly (60). Trigger assembly (150) of the present example comprises a pivotable attachment arm (152) that may be pivoted about a pin (not shown), a trigger arm (154), an intermediate link (156), and an actuation arm (158). Actuation arm (158) is coupled to a trigger yoke (170) at the distal end of actuation arm (158). Actuation arm (158) comprises one or more mounting pins (160) extending outwardly from actuation arm (158) and pins (160) are sized to be slidably received in corresponding elongated channel (162) formed in cover (61). Accordingly, when trigger (68) is pivoted proximally from the open position to the closed position attachment arm (152) and trigger arm (154) pivot within multi-piece handle assembly (60). Intermediate link (156) coupled to trigger arm (154) transfers this pivoting motion from trigger arm (154) to actuation arm (158) to slidably translate actuation arm (158) proximally via pins (160) within channel (162). Trigger yoke (170), which is coupled to actuation arm (158), is translated proximally as well. In the present example, trigger yoke (170) is coupled to a force-limiting mechanism (180), which is further coupled to transmission assembly (70) as will be described in more detail below, to operate inner tubular actuating member (74). A cavity (140), shown in FIG. 2, is configured to receive transducer (100) therein from a transducer aperture (142) formed in cover (61). Cavity (140) is configured to receive at least a portion of transducer (100) therein such that transducer (100) and transmission assembly (70) may be coupled together. Still other configurations for multi-piece handle assembly (60) will be apparent to one of ordinary skill in the art in view of the teachings herein.

B. Exemplary Transducer

Figure 3:
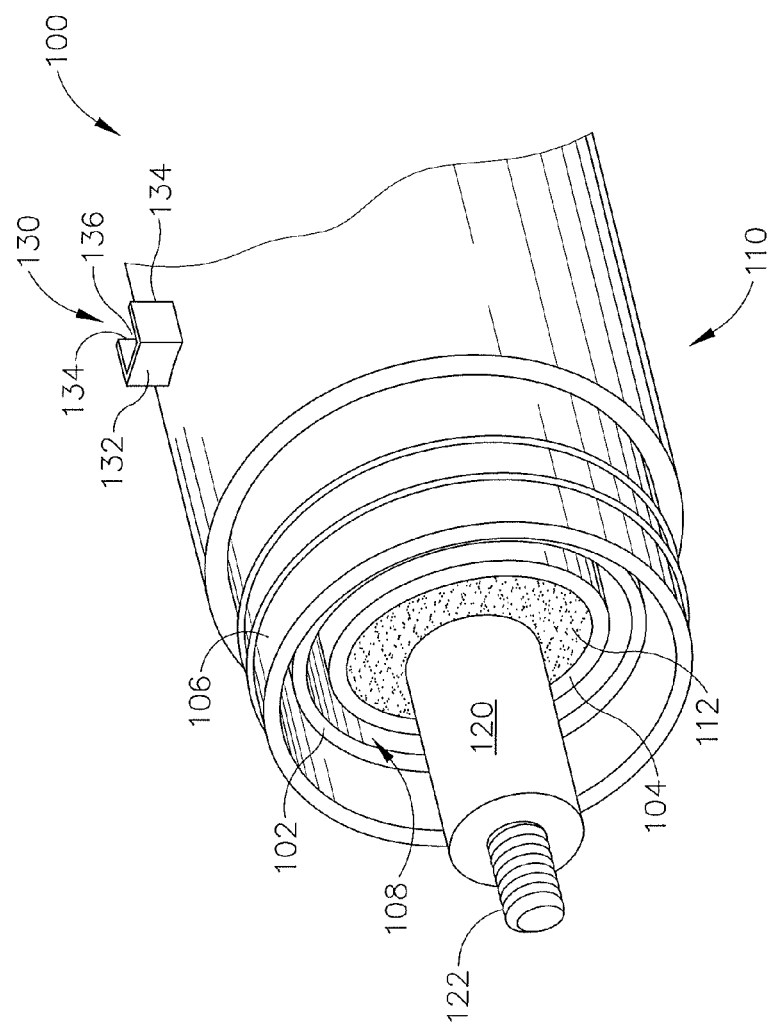
FIG. 3 depicts a partial perspective view of a distal end of an exemplary transducer.

As shown in FIG. 3, transducer (100) of the present example is a tubular component that is coupled to generator (20) via cable (30), though it should be understood that transducer (100) may be a cordless transducer. For instance, transducer (100) may instead receive power from a power source that is contained within handle assembly (60), in accordance with the teachings of various references cited herein or otherwise. In the present example, transducer (100) includes a first conductive ring (102) and a second conductive ring (104) which are disposed within a body (110) of transducer (100). A transducer extension (130) extends outwardly from body (110) and has a pair of sidewalls (134) and, optionally, a wall (132). Sidewalls (134) and wall (132) form an engagement region (136) to engage transducer tab (310) of slider (300), as will be described in more detail below with reference to FIGS. 5A-5C. Transducer extension (130) of the present example restricts rotational and, optionally, proximal longitudinal movement of transducer (100) when slider (300) is in a locked position, as will be discussed below. In the present example, first conductive ring (102) comprises a ring member having one or more electrical contacts that are disposed on the ring member and that are configured to electrically couple first conductive ring (102) to a power source. First conductive ring (102) is disposed between body (110) and a horn (120) extending distally from body (110). Horn (120) comprises distal horn threads (122) such that horn (120) is coupleable to waveguide (210), as will be discussed below in reference to FIG. 4. First conductive ring (102) of the present example is coaxial with and adjacent to a flange (106). Flange (106) of the present example is configured to further mechanically couple transducer (100) within multi-piece handle assembly (60). A transducer cavity (108) is disposed between first conductive ring (102) and a second conductive ring (104) such that first conductive ring (102) is electrically isolated from second conductive ring (104) and/or other conductive components of transducer (100). First conductive ring (102) is located on a non-conductive platform extending distally from body (110). First conductive ring (102) is electrically coupled to cable (30), shown in FIG. 1, by one or more electrical wires or conductive etchings (not shown) within body (110). Such electrical coupling of first conductive ring (102) to cable (30) may include a slip ring to facilitate free rotation of transducer (100) relative to cable (30).

Second conductive ring (104) of transducer (100) similarly comprises a ring member that is disposed between body (110) and horn (120). Second conductive ring (104) is disposed between first conductive ring (102) and horn (120). As is shown in FIG. 3, first and second conductive rings (102, 104) are coaxial members. Second conductive ring (104) is likewise electrically isolated from first conductive ring (102) and other conductive components of transducer (100). Similar to first conductive ring (102), second conductive ring (104) extends from the non-conductive platform. One or more washer-shaped spacers (112) may be disposed between second conductive ring (104) and horn (120) to isolate the vibrations transmitted through horn (120) from the other components of transducer (100). Second conductive ring (104) is also electrically coupled to cable (30), shown in FIG. 1, by one or more electrical wires or conductive etchings (not shown) within body (110). Such electrical coupling of second conductive ring (104) to cable (30) may also include a slip ring to facilitate free rotation of transducer (100) relative to cable (30). One merely exemplary suitable ultrasonic transducer (100) is Model No. HP054, sold by Ethicon Endo-Surgery, Inc. of Cincinnati, Ohio, though it should be understood that any other suitable transducer may be used.

As shown in the present example, the distal end of transducer (100) threadably couples to the proximal end of a transmission assembly via horn (120). The distal end of transducer (100) also interfaces with one or more electrical connections (not shown) via first and second conductive rings (102, 104) to electrically couple transducer (100) to toggle buttons (69) to provide a user with finger-activated controls for activating transducer (100) while using surgical instrument (50). The interface between the one or more electrical connections and the first and second conductive rings (102, 104) may include a slip ring connection to permit free rotation of transducer (100) relative to multi-piece handle assembly (60). Still other configurations for transducer (100) will be apparent to one of ordinary skill in the art in view of the teachings herein. For instance, first and second conductive rings (102, 104) may be omitted from the distal end of transducer (100) and the electrical coupling of transducer (100) to toggle buttons (69) may be accomplished by alternative structures, such as conductors at the proximal end of transducer (100), conductors located along the side of body (110) of transducer (100), directly from cable (30), and/or otherwise. When transducer (100) of the present example is activated via a toggle button (69), transducer (100) is operable to create mechanical energy in the form of linear oscillations or vibrations, at an ultrasonic frequency (such as 55.5 kHz). By way of example only, such oscillations or vibrations may be torsional or transverse vibrations relative to transducer (100). When transducer (100) is coupled to transmission assembly (70) via horn (120), these mechanical oscillations are transmitted through the internal waveguide of transmission assembly (70) to end effector (80). In the present example, with blade (82) being coupled to the waveguide, blade (82) thereby oscillates at the ultrasonic frequency. Thus, when tissue is secured between blade (82) and clamp arm (84), the ultrasonic oscillation of blade (82) may simultaneously sever tissue and denature the proteins in adjacent tissue cells, thereby providing a coagulative effect with relatively little thermal spread. An electrical current may also be provided through blade (82) and clamp arm (84) to cauterize the tissue. While some configurations for transducer (100) have been described, still other suitable configurations for transducer (100) will be apparent to one or ordinary skill in the art in view of the teachings herein.

C. Exemplary Transmission Assembly for Threaded Attachment

As noted previously, in some instances it may be useful to detach transmission assembly (70) from multi-piece handle assembly (60) and transducer (100). Merely exemplary instances include the use of multi-piece handle assembly (60) with multiple transmission assemblies (70) having different sized and/or shaped blades (82), use with various end effectors (80) with entirely different functions and/or modalities (e.g., RF end effectors, stapling end effectors, cutting end effectors, etc.), or for reuse of a single multi-piece handle assembly (60) for multiple operations by a user. Accordingly, a version permitting the user to swap transmission assemblies (70) with multi-piece handle assembly (60) may be useful. In some versions, transducer (100) may be replaced with other mechanical devices, such as a motors, pneumatics, etc., that produce oscillations or other forms of motion that are transmittable through transmission assembly (70) to end effector (80). By way of example only, end effector (80) may lack a harmonic blade and may instead include features actuated by rotary motion produced by a motor that is used in place of transducer (100).

Figure 4:
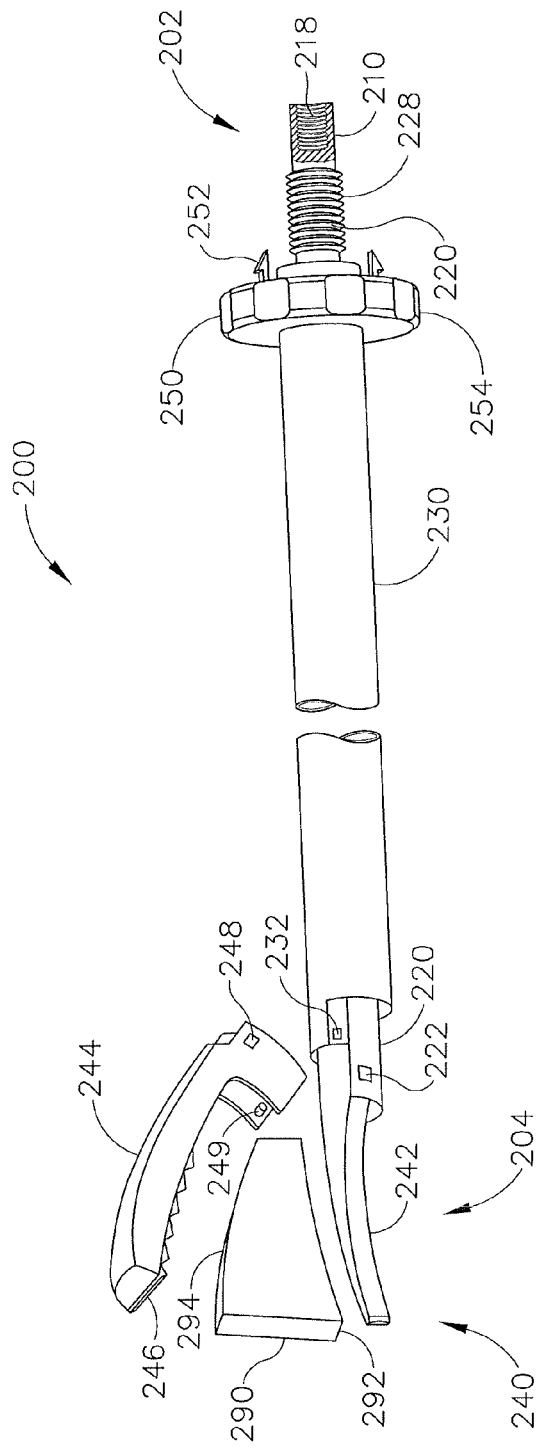
FIG. 4 depicts a perspective view of an exemplary transmission assembly.

One merely exemplary transmission assembly (200) is shown in FIG. 4 having a proximal end (202), a distal end (204), a waveguide (210), an inner tubular actuating member (220), an outer sheath (230), and an end effector (240) at the distal end of transmission assembly (200). In the present example, waveguide (210), inner tubular actuating member (220), and outer sheath (230) are coaxial members with waveguide (230) in the center, inner actuating member (220) disposed about waveguide (210), and outer sheath (230) disposed about inner actuating member (220).

Referring to distal end (204) of transmission assembly (200) first, end effector (240) comprises a blade (242), a clamp arm (244), and one or more optional clamp pads (246). In the present example, blade (242) is coupled to waveguide (210) such that the mechanical vibrations transmitted to waveguide (210) from transducer (100) are also transmitted to blade (242). Merely exemplary couplings for blade (242) to waveguide (210) include welding blade (242) to waveguide (210), integrally forming blade (242) with waveguide (210), mechanically or chemically coupling blade (242) to waveguide (210), and/or any other suitable configuration as will be apparent to one of ordinary skill in the art in view of the teachings herein. In some versions, blade (242) is a curved blade, such as blade (242) shown in FIG. 4; and in some versions blade (242) may be a straight blade. Furthermore, blade (242) may have a variety of shapes and sizes. In the present example, blade (242) is a tapered rectangular blade, though it should be understood that blade (242) may be cylindrical, triangular, hemi-cylindrical, square, hooked, and/or any other shape for blade (242). Furthermore, additional features may be added to blade (242), including spherical tips, hooked tips, square tips, serrated edging, and/or any other additional features. Still other configurations for blade (242) will be apparent to those of ordinary skill in the art in view of the teachings herein.

Clamp arm (244) of the present example is a curved member that corresponds to the curvature of blade (242). Clamp arm (244) may optionally include clamp pads (246) to grip or secure tissue against blade (242). Such clamp pads may be configured in accordance with at least some of the teachings of U.S. Pat. Pub. No. 2006/0079874, entitled "Tissue Pad for Use with an Ultrasonic Surgical Instrument," published Apr. 13, 2006. Pivotal movement of clamp arm (244) with respect to blade (242) is accomplished by a first pair of pivot points (248) on clamp arm (244) that pivotally couple to outer sheath (230) and a second set of pivot points (249) on clamp arm (244) that pivotally couple to inner tubular actuating member (220). In the present example, outer sheath (230) is coupleable to multi-piece handle assembly (60) through a rotation knob (250), thereby mechanically grounding outer sheath (230). First set of pivot points (248) of clamp arm (244) are pivotally connected to outer sheath (230) via corresponding through holes (232) on outer sheath (230). In some versions, first set of pivot points (248) comprise through holes and a securing pin or rivet may be inserted through first set of pivot points (248) and through through holes (232) to secure clamp arm (244) to outer sheath (230). The pin in this version may be laser welded to clamp arm (244) or the pin may be laser welded to outer sheath (230). Of course through holes (232) may instead be outwardly extending pins and first set of pivot points (248) may be through holes. Still other configurations for first set of pivot points (248) and through holes (232) will be apparent to one of ordinary skill in the art in view of the teachings herein.

Second set of pivot points (249) of clamp arm (244) are pivotally connected to inner tubular actuating member (220) via corresponding through holes (222) on inner tubular actuating member (220). In some versions, second set of pivot points (249) comprise through holes and a securing pin or rivet may be inserted through second set of pivot points (249) and through through holes (222) to secure clamp arm (244) to inner tubular actuating member (220). The pin in this version may be laser welded to clamp arm (244) or the pin may be laser welded to inner tubular actuating member (220). Of course through holes (222) may instead be outwardly extending pins and second set of pivot points (249) may be through holes. Still other pivotable configurations for second set of pivot points (249) and through holes (222) will be apparent to one of ordinary skill in the art in view of the teachings herein. For instance, clamp arm (244) may be configured in accordance with at least some of the teachings of U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein.

With clamp arm (244) so secured to outer sheath (230) and inner tubular actuating member (220), clamp arm (244) is pivotable when inner tubular actuating member (220) translates longitudinally. In the present example, inner tubular actuating member (220) is translatable relative to the longitudinal axis of outer sheath (230) and is coupled to force-limiting mechanism (180) within multi-piece handle assembly (60). Thus, when force-limiting mechanism (180) translates via trigger (68) and trigger assembly (150), clamp arm (244) is pivotable from an open position to a closed position. It should be understood that, as with other components referred to herein, clamp arm (84, 244) is merely optional. Likewise, trigger (68) and trigger assembly (150) and the components described herein for pivoting clamp arm (84, 244) are also merely optional. Thus, some versions of end effector (80, 240) may simply consist of a blade (82, 842) and/or other features.

As shown in FIG. 4, a spacer (290) is insertable between clamp arm (244) and blade (242) to maintain clamp arm (244) in the open position. Spacer (290) has a flat bottom surface (292) and an angled top surface (294) in this example. Top surface (294) is set at an angle to maintain clamp arm (244) in the open position relative to blade (242) when bottom surface (292) abuts blade (242). In some versions, bottom surface (292) may be configured to snap or clip onto blade (242) to secure spacer (290) relative to blade (242). Alternatively, a recess may be provided in spacer (290) such that spacer (290) may be slid onto blade (242). Further still, an adhesive may be applied to bottom surface (292) and/or top surface (294) to also secure spacer (290). Thus, when spacer (290) is inserted between clamp arm (244) and blade (242), clamp arm (244) is prevented from pivoting to a closed position. This may permit a user to couple transmission assembly (200) to multi-piece handle assembly (60) while maintaining both clamp arm (244) and trigger (68) in their respective open positions.

Referring now to proximal end (202) of transmission assembly (200), a rotation knob (250) couples outer sheath (230) to multi-piece handle assembly (60). In the present example, rotation knob (250) comprises an inner ring portion (not shown) having one or more connectors (252) extending proximally therefrom, an outer ring (254), and a pin (not shown) extending through outer ring (254), outer sheath (230), inner tubular actuating member (220), and waveguide (210). Accordingly, when outer ring (254) of rotation knob (250) is rotated, waveguide (210), inner tubular actuating member (220), and outer sheath (230) also rotate. Inner ring portion and outer ring (254) of the present example are complementary bearing components such that outer ring (254) is rotatable relative to inner ring portion. It should be understood that the pin does not extend though inner ring portion. As previously noted, inner ring portion includes connectors (252). In the present example connectors (252) are shown as snap-fit connectors, though other suitable connecting features, such as threading, adhesives, pins, clips, snaps, and/or other connectors may be used as will be apparent to one of ordinary skill in the art in view of the teachings herein. When transmission assembly (200) is assembled with multi-piece handle assembly (60) and transducer (100), as will be discussed below, connectors (252) of the present example insert into one or more recesses (not shown) and couple rotation knob (250) to cover (61) of multi-piece handle assembly (60). A release mechanism, such as a push button (not shown) on multi-piece handle assembly (60) or on rotation knob (250) may be provided to decouple connectors (252) from cover (61) when transmission assembly (200) is to be removed. Alternatively, connectors (252) may be designed to break-away when transmission assembly (200) is decoupled. Further still, if threading is used, inner portion of rotation knob (250) may be rotated to decouple from multi-piece handle assembly (60). Still other suitable configurations for rotation knob (250) will be apparent to one of ordinary skill in the art in view of the teachings herein.

Still referring to proximal end (202) of transmission assembly (200), external threads (228) are included at the proximal end of inner tubular actuating member (220) as shown in FIG. 4. External threads (228) screw into complementary threads (not shown) of force-limiting mechanism (180), which is in turn driven by trigger assembly (150). Additionally, a recess having internal threading (218) is included at the proximal end of waveguide (210) as shown in FIG. 4. Internal threading (218) screws onto horn threads (122) to mechanically and acoustically couple waveguide (210) to transducer (100). It should be understood that external threads (228) need not threadably couple to force-limiting mechanism (180) contemporaneously with internal threading (218) threadably coupling to horn threads (122). Further still, it should be understood that transmission assembly (200) may be held in a fixed position while multi-piece handle assembly (60) is threaded onto transmission assembly (200) by rotating assembly (60) relative to assembly (200). Other suitable configurations for transmission assembly (200) will be apparent to one of ordinary skill in the art in view of the teachings herein. Similarly, various other suitable ways in which transmission assembly (200) may be coupled with handle assembly (60) will be apparent to those of ordinary skill in the art in view of the teachings herein.

Figure 5A:
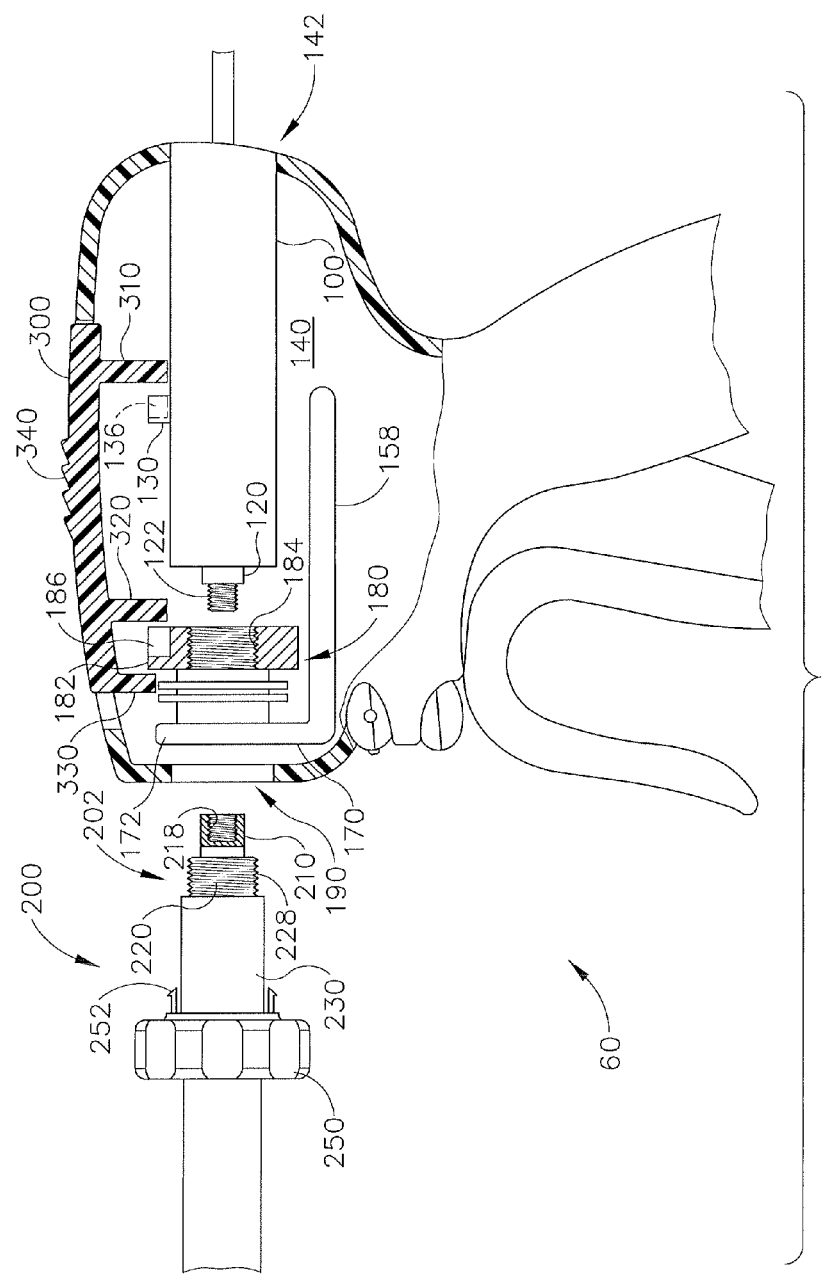
FIG. 5A depicts a partial side cross-sectional view of an assembly of a surgical instrument including the multi-piece handle assembly of FIG. 2, the transducer of FIG. 3, and the transmission assembly of FIG. 4.
Figure 5B:
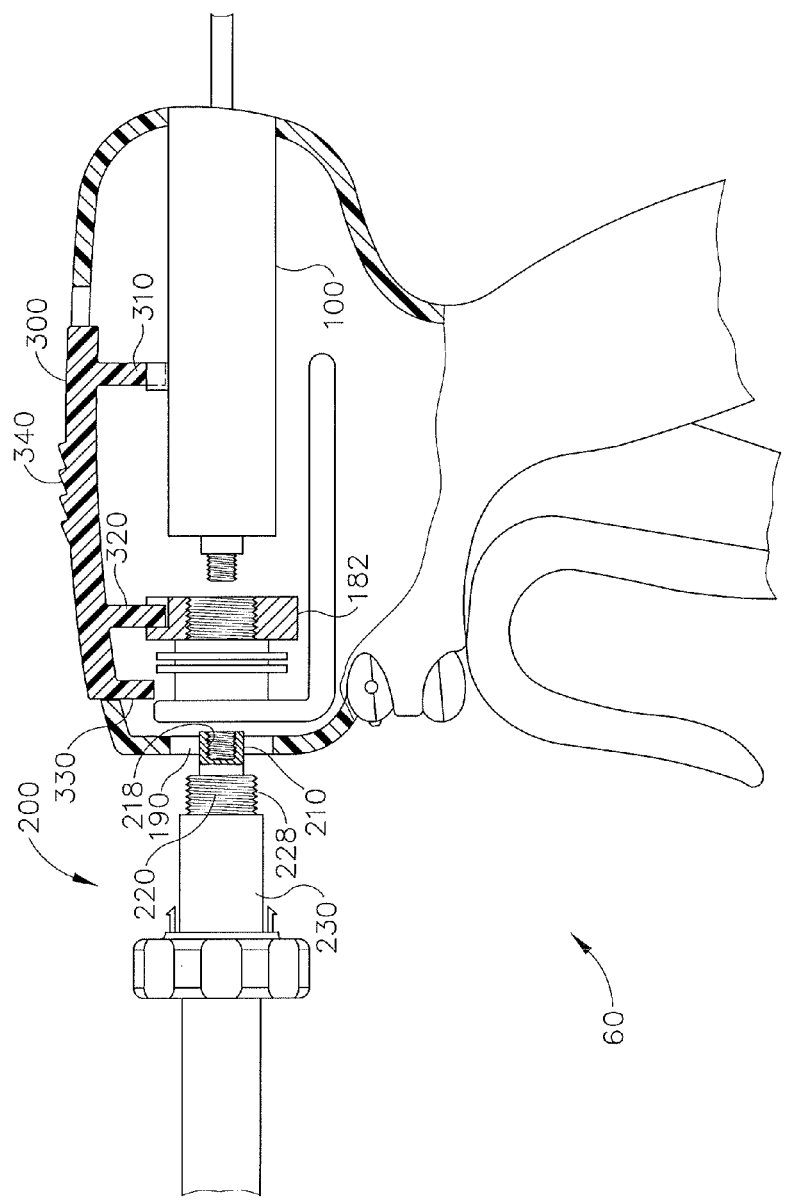
FIG. 5B depicts a partial side cross-sectional view of the assembly of FIG. 5A with an exemplary slide button assembly in a locked position.
Figure 5C:
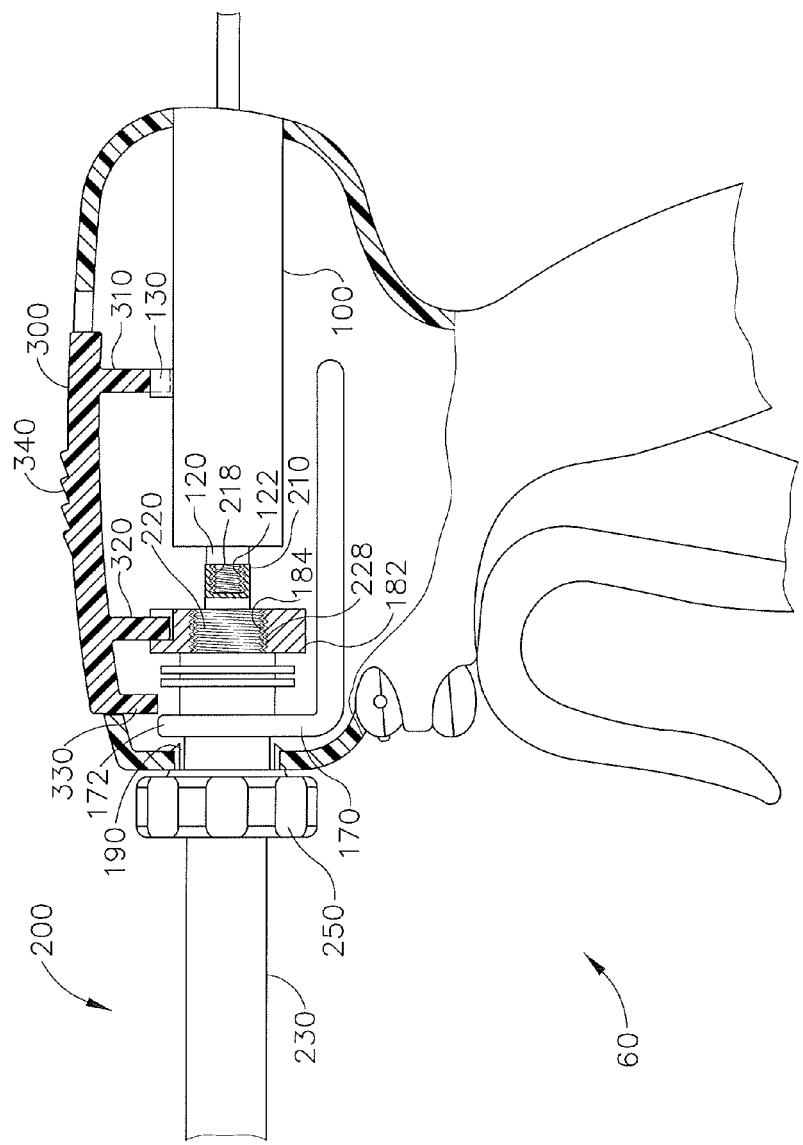
FIG. 5C depicts a partial side cross-sectional view of the assembly of FIG. 5A with the transmission assembly, the transducer, and a threaded member coupled together.

D. Exemplary Threaded Assembly of Transmission Assembly, Multi-Piece Handle Assembly, and Transducer FIGS. 5A-5C show the coupling of transmission assembly (200) to transducer (100) and a portion of multi-piece handle assembly (60) for surgical instrument (50). FIG. 5A shows proximal end (202) of transmission assembly (200) aligned for insertion and coupling with multi-piece handle assembly (60) and transducer (100). As discussed above, transmission assembly (200) of the present example comprises a rotation knob (250) having connectors (252), an outer sheath (230), an inner tubular actuating member (220) having external threads (228), and a waveguide (210) having a recess with internal threading (218).

Multi-piece handle assembly (60) of the present example has a transmission aperture (190), an actuation arm (158) coupled to a trigger yoke (170), a force-limiting mechanism (180) coupled to the trigger yoke (170), a threaded member (182) coupled to the force-limiting mechanism (180), a slider (300), and a transducer aperture (142). Some components of multi-piece handle assembly (60) have been omitted from FIGS. 5A-5C to provide a better view of the coupling of transmission assembly (200) with transducer (100) and threaded member (182). Transmission aperture (190) is configured to receive proximal end (202) of transmission assembly (200). In the present example, transmission aperture (190) is a circular opening sized to receive outer sheath (230). Optionally, a seal or grommet may be included with transmission aperture (190) to fluidly seal outer sheath (230) to multi-piece handle assembly (60) when transmission assembly (200) is inserted therein. In addition, if rotation knob (250) is included with transmission assembly (200), one or more recesses (not shown) may be formed in cover (61) of multi-piece handle assembly (60) near transmission aperture (190). Such one or more recesses may be configured to receive connectors (252) of inner ring portion of rotation knob (250) to couple rotation knob (250) to multi-piece handle assembly (60), as described above.

Figure 10:
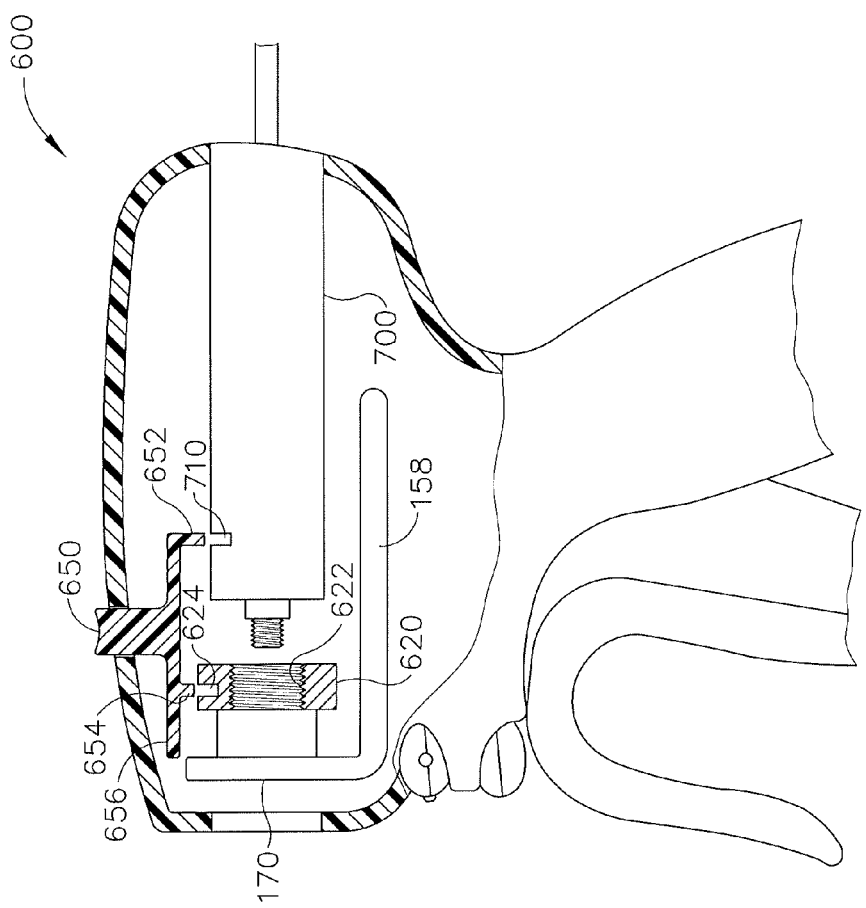
FIG. 10 depicts a partial cross-sectional view of an exemplary alternative push button.

As described previously, actuation arm (158) is coupled to trigger yoke (170) such that trigger yoke (170) is translatable longitudinally when trigger (68) is pivoted. Trigger yoke (170) includes an upper portion (172) configured to engage a trigger tab (330) on slider (300), as will be described later in more detail. As shown in FIG. 5A, trigger yoke (170) is coupled to force-limiting mechanism (180) and threaded member (182) is coupled to force-limiting mechanism (180). Accordingly, when trigger yoke (170) is actuated via trigger (68), force-limiting mechanism (180) and threaded member (182) are also actuated. It should be understood that force-limiting mechanism (180) is merely optional and threaded member (180) may be coupled directly to trigger yoke (170) (as shown in FIG. 10). In addition, force-limiting mechanism (180) and threaded member (182) are configured to freely rotate relative to trigger yoke (170) and relative to multi-piece handle assembly (60) when slider (300) is not engaged with threaded member (182). Threaded member (182) of the present example comprises threads (184) that complement external threads (228) on the proximal end of inner tubular actuating member (220). Threaded member (182) also has an engagement portion (186) configured to engage with actuation tab (320) of slider (300), as will be described in more detail below. Thus, when transmission assembly (200) is to be coupled to multi-piece handle assembly (60), external threads (228) engage complementary threads (184) to couple inner tubular actuating member (220) to threaded member (182). As a result, when trigger (68) is pivoted, inner tubular actuating member (220) is actuated via the coupling with threaded member (182), and clamp arm (244) is thereby pivoted to clamp onto tissue.

Transducer aperture (142) formed in the proximal end of multi-piece handle assembly (60) is size to receive a portion of transducer (100) therein. Transducer (100) is insertable into cavity (140) of multi-piece handle assembly (60) with horn (120) located proximal to threaded member (182). Transducer (100) may be manually held in place by a user during assembly of surgical instrument (50) or transducer (100) may be secured via one or more clips or retaining features (not shown) such that transducer (100) has limited longitudinal and/or rotational movement while transmission assembly (200) is coupled to transducer (100). For instance, transducer extension (130) of the present example includes a wall (132) and sidewalls (134) (shown in FIG. 3) with which transducer tab (310) of slider (300) engages. Transducer extension (130) may further include resilient snaps (not shown) that may be configured to snap onto transducer tab (310) to both retain slider (300) in the locked position and to limit the longitudinal and/or rotational movement of transducer (100). When transducer (100) is initially inserted into multi-handle piece assembly (60), transducer (100) may be rotated such that transducer extension (130) does not snag on transducer tab (310). Transducer (100) is then rotated to align transducer tab (310) for engagement with transducer extension (130) once transducer extension (130) is distal of transducer tab (310). For instance, an indicator on the proximal end of transducer (100) may be configured to align with a complementary indicator on multi-piece handle assembly (60) to provide feedback to the user that transducer extension (130) is aligned with transducer tab (310). Alternatively, an aperture in multi-piece handle assembly (60) may be aligned with an indicator on the side of transducer (100) to provide visual confirmation of alignment of transducer extension (130) with transducer tab (310). If transducer extension (130) includes snap features, the user may need to actuate slider (300) to disengage the snap features from transducer tab (310) to actuate slider (300) into an unlocked position. In one alternative version, shown in FIG. 6, transducer extension (130) is engaged by proximal movement of a slider (350) such that transducer (100) need not be rotated to avoid snagging on transducer tab (360), as will be discussed below in greater detail. In some versions, a slot (144) may be formed in casing (61) such that a user aligns transducer extension (130) with slot (144) to insert transducer (100). The alignment of transducer extension (130) with slot (144) may also align transducer extension (130) with transducer tab (360). Still other configurations for transducer (100) will be apparent to one of ordinary skill in the art in view of the teachings herein.

Slider (300) of the present example is translatable longitudinally relative to casing (61) of multi-piece handle assembly (60) and is configured to engage portions of trigger yoke (170), threaded member (182), and transducer (100) when slider (300) is in a locked position (shown in FIGS. 5B-5C). Slider (300) shown in FIG. 5A is in an unlocked position and includes a transducer tab (310), an actuator tab (320), and a trigger tab (330). Slider (300) of the present example also includes a grip portion (340) to aid a user in moving slider (300) between a locked and unlocked position, though it should be understood that grip portion (340) is merely optional. Transducer tab (310), actuator tab (320), and trigger tab (330) of the present example each extends downwardly from slider (300), though transducer tab (310), actuator tab (320), and trigger tab (330) may extend at alternative angles depending on the orientation and position of slider (300) relative to multi-piece handle assembly (60). Transducer tab (310) is configured to engage with engagement portion (136) of transducer extension (130). Actuator tab (320) is configured to engage with engagement portion (186) of threaded member (182). Trigger tab (330) is configured to abut a proximal portion of upper portion (172) of trigger yoke (170).

Accordingly, when slider (300) is translated distally into the locked position shown in FIG. 5B, transducer tab (310), actuator tab (320), and trigger tab (330) each engage transducer (100), threaded member (182), and trigger yoke (170), respectively, to restrict those components' movement. In some versions, trigger tab (330) may be omitted (e.g., if force-limiting mechanism (180) is rotationally and/or longitudinally constrained via the coupling to trigger (68)). With slider (300) in the locked position, transmission assembly (200) is inserted into transmission aperture (190) to screw inner tubular actuating member (220) into threaded member (182) and waveguide (210) onto transducer (100), as shown in FIG. 5C. The coupling of transmission assembly (200) may be accomplished using a torque limiting device (not shown) to couple transmission assembly (200) to threaded member (182) and transducer (100) without over tightening those connections. In some versions, the torque limiting device is incorporated into rotation knob (250). If rotation knob (250) is provided, connectors (252) on inner ring portion may also engage the one or more recesses in cover (61) of multi-piece handle assembly (60) to couple rotation knob (250) thereto. Once transmission assembly (200) is coupled to threaded member (182) and transducer (100), slider (300) may be slid back to the unlocked position. In some versions, slider (300) may have a return spring (not shown) to urge slider (300) towards the unlocked position. Alternatively, the return spring may be omitted and the user manually translates slider (300) between the locked and unlocked positions. In some other versions, transducer tab (310), actuator tab (320), and/or trigger tab (330) may be on separate sliders such that each tab (310, 320, 330) or a combination of tabs is actuatable relative to the others. For instance, in some versions actuator tab (320) and transducer tab (310) are on separate sliders such that a user can selectively engage actuator tab (320) with force-limiting mechanism (180) and transducer tab (310) with transducer extension (130). Accordingly, inner tubular actuating member (220) may be screwed into threaded member (182) separately from the engagement of waveguide (210) onto transducer (100).

As will be appreciated by one of ordinary skill in the art in view of the teachings herein, when transducer tab (310) and transducer extension (130) are engaged in the locked position, the rotational and/or proximal longitudinal movement of transducer (100) is restricted by sidewalls (134) and/or wall (132). When transducer tab (310) and transducer extension (130) are not engaged, the rotational and/or proximal longitudinal movement of transducer (100) is not restricted and transducer (100) is permitted to freely rotate relative to multi-piece handle assembly (60). Such rotation may be accomplished via rotation knob (250). Likewise, when actuator tab (320) and engagement portion (186) of threaded member (182) are engaged in the locked position, the rotational movement of threaded member (182) is also restricted. When actuator tab (320) and engagement portion (186) of threaded member (182) are not engaged, the rotational movement of threaded member (182) is not restricted and threaded member (182) is also permitted to freely rotate relative to multi-piece handle assembly (60). Such rotation may also be accomplished via rotation knob (250). When trigger tab (330) and upper portion (172) of trigger yoke (170) are engaged in the locked position, the longitudinal movement of trigger yoke (170) is restricted as well. Thus, with spacer (290) inserted between blade (242) and clamp arm (244) of transmission assembly (200) and trigger (68) immobilized in the open position via trigger tab (330) engaging trigger yoke (170), transmission assembly (200) can be coupled to multi-piece handle assembly (60) while maintaining both trigger (68) and clamp arm (244) in their respective open positions during assembly. When trigger tab (330) and upper portion (172) of trigger yoke (170) are not engaged, the longitudinal movement of trigger yoke (170) is not restricted such that trigger (68) may be used to pivot clamp arm (244) to clamp tissue.

When a user is finished using surgical instrument (50) or if the user desires to use a different transmission assembly (200), the user may detach transmission assembly (200) by translating slider (300) to the locked position and unscrewing transmission assembly (200) from threaded member (182) and transducer (100). Transmission assembly (200) may be then be disposed of, cleaned for reuse, reclaimed for reprocessing and/or otherwise. In addition, multi-piece handle assembly (60) and/or transducer (100) may also be disposed of, cleaned for reuse, reclaimed for reprocessing and/or otherwise. Accordingly, a detachable transmission assembly (200) may permit a user to use or reuse multi-piece handle assembly (60) multiple times or with multiple transmission assemblies (200). While some merely exemplary configurations for multi-piece handle assembly (60), transmission assembly (200), and transducer (100) have been described, still other suitable configurations will be apparent to one of ordinary skill in the art in view of the teachings herein.

Figure 6:
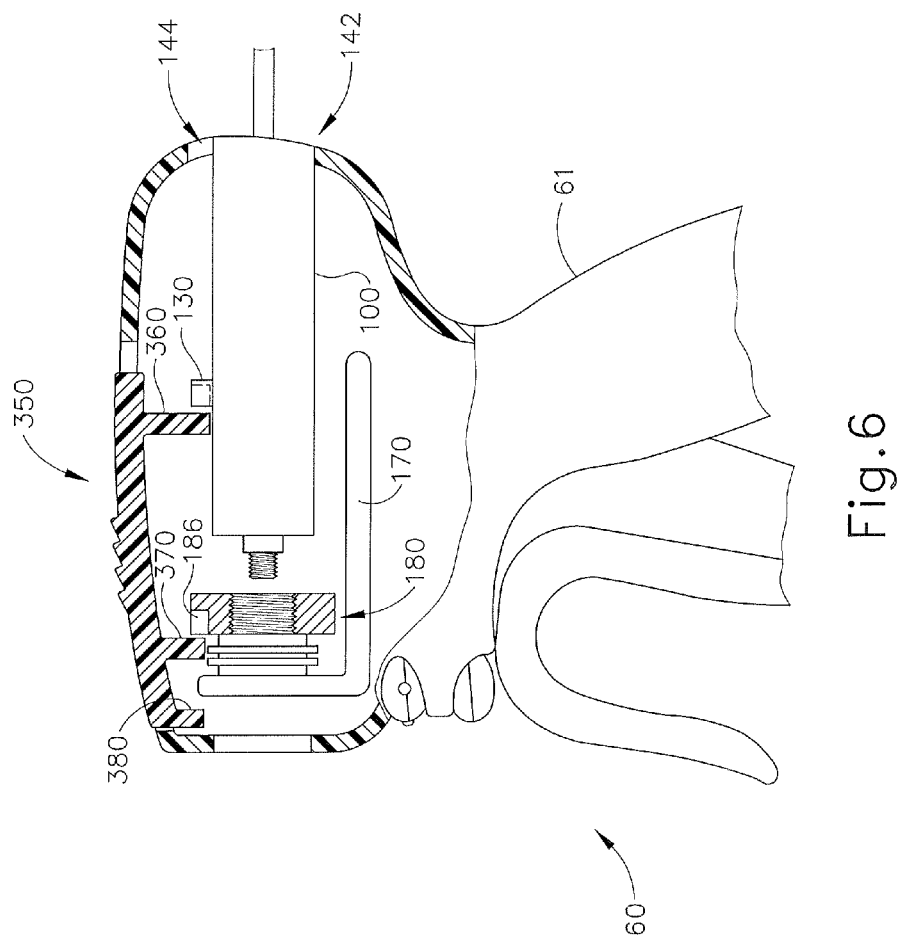
FIG. 6 depicts a partial side cross-sectional view of an alternative multi-piece handle assembly having a distally actuatable slider.

FIG. 6 depicts an exemplary alternative slider (350) for use with transducer (100), force-limiting mechanism (180), and trigger yoke (170). Slider (350) includes a transducer tab (360), an actuation tab (370), and a trigger tab (380) similar to slider (300). In the present example, slider (350) is configured to actuate proximally to selectively engage and lock transducer (100), force-limiting mechanism (180), and/or trigger yoke (170). It should be understood that in this example, trigger yoke (170) is actuated distally such that the trigger (not shown) is in the closed position. Accordingly, when a transmission assembly, such as transmission assembly (200), is coupled to transducer (100) and/or force-limiting mechanism (180), the clamp arm is closed against the blade to maintain the alignment with the trigger. When a user desires to couple the transmission assembly, the user initially inserts transducer (100) into multi-piece handle assembly (60). In the example shown, transducer extension (130) is inserted through slot (144) to align transducer extension (130) with transducer tab (360). With transducer (100) inserted, the user actuates slider (350) proximally to engage transducer tab (360) with transducer extension (130), actuation tab (370) with engagement portion (186), and trigger tab (380) with trigger yoke (170). The user then couples the transmission assembly to force-limiting mechanism (180) and/or transducer (100). The user may then actuate slider (350) distally to an unlocked position. In such a position, transducer tab (360) is disengaged from transducer extension (130), actuation tab (370) is disengaged from engagement portion (186), and trigger tab (380) is disengaged from trigger yoke (170). Transducer (100), force-limiting mechanism (180), and/or the transmission assembly may then rotate relative to multi-piece handle assembly (60).

E. Exemplary Latch Assembly

Figure 7:
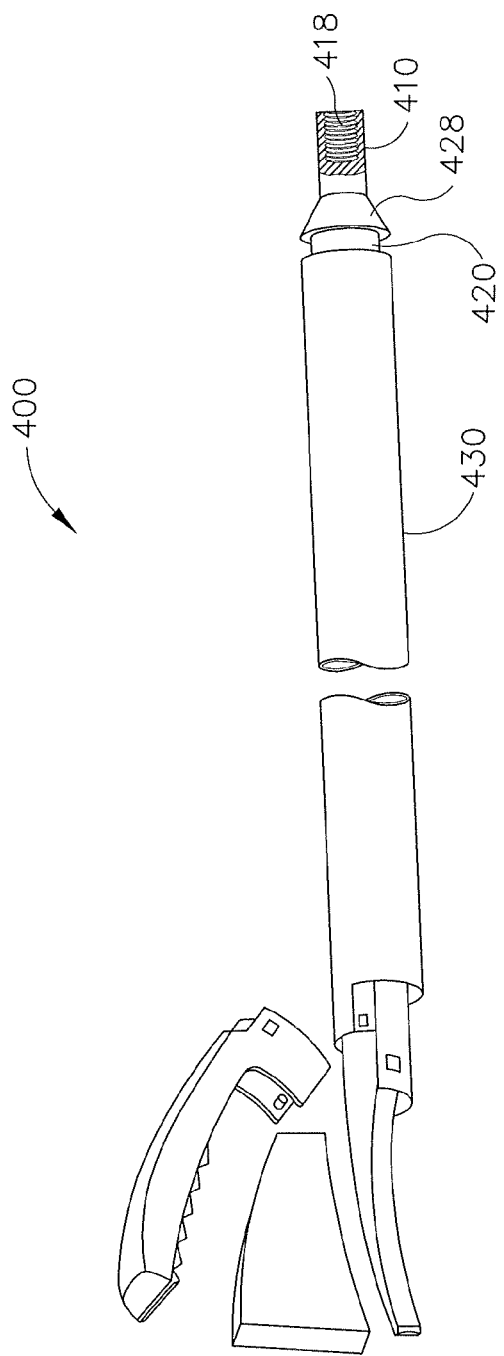
FIG. 7 depicts a perspective view of an exemplary alternative transmission assembly.

FIGS. 7-9B show one exemplary alternative transmission assembly (400) and multi-piece handle assembly (500). Alternative transmission assembly (400), shown in FIG. 7, is configured in a substantially similar manner as transmission assembly (200) described above. However, inner tubular actuating member (420) of the present example comprises one or more flared portions (428) instead of external threads (228) of transmission assembly (200). In the present example, flared portion (428) is a frusto-conical portion that forms a uniform flare about the circumference of inner tubular actuating member (420). It should be understood that flared portion (428) may alternatively comprises discrete flared portions distributed about the circumference of inner tubular actuating member (420). For instance, one, two, three, or four discrete flared portions may be included. Similar to transmission assembly (200), transmission assembly (400) also comprises an outer sheath (430) and a waveguide (410) having inner threading (418) that is complementary to horn threads (122) on horn (120) of transducer (100).

Figure 8A:
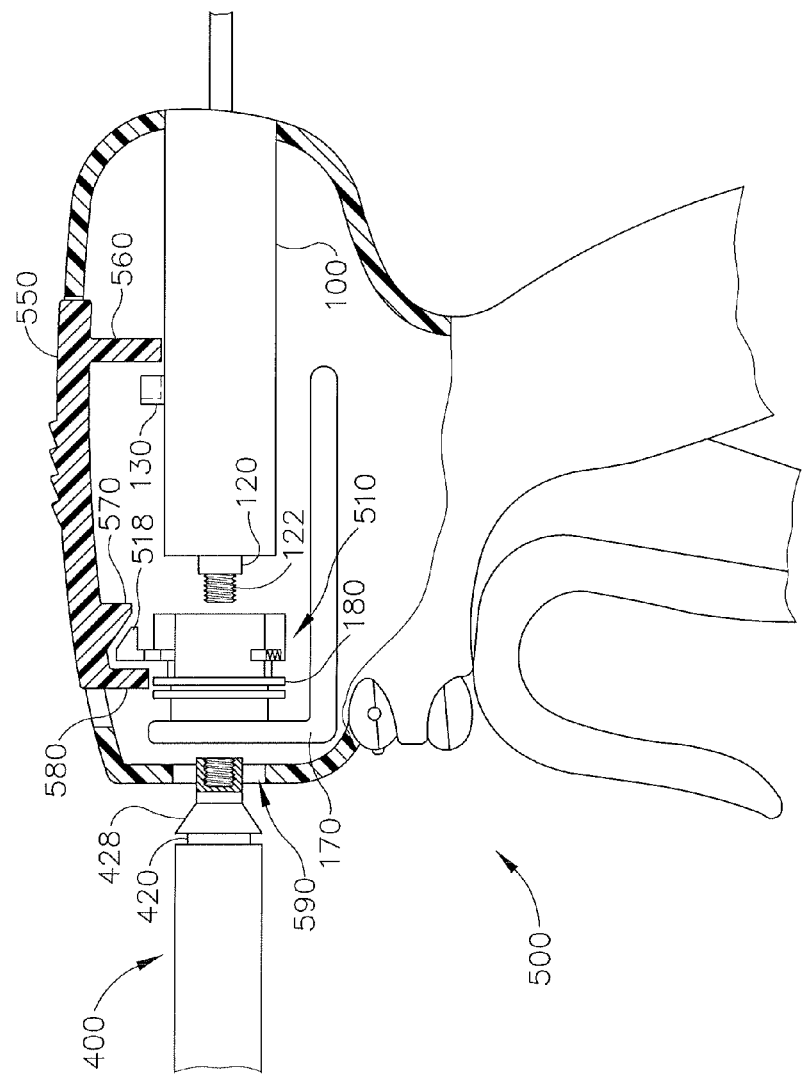
FIG. 8A depicts a partial side cross-sectional view of an exemplary alternative assembly of a surgical instrument including an exemplary alternative multi-piece handle assembly, the transducer of FIG. 3, and the transmission assembly of FIG. 7.
Figure 8B:
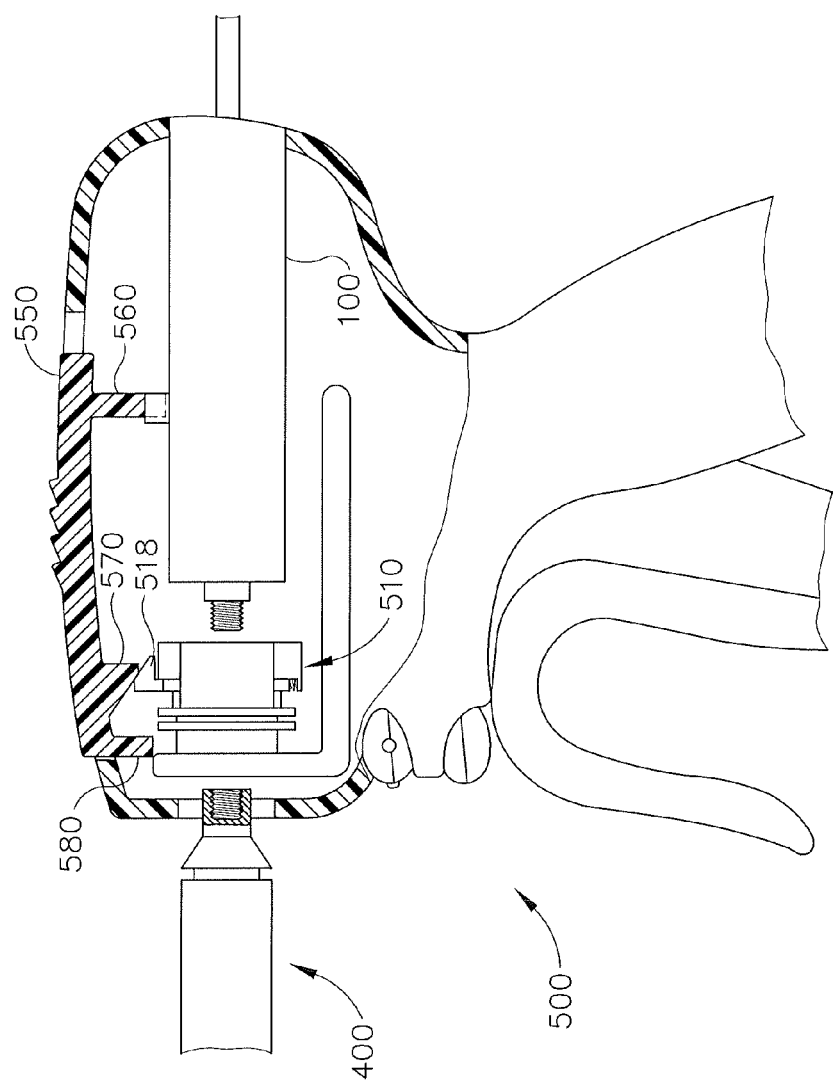
FIG. 8B depicts a partial side cross-sectional view of the assembly of FIG. 8A with an exemplary alternative slide button assembly in a locked position.
Figure 8C:
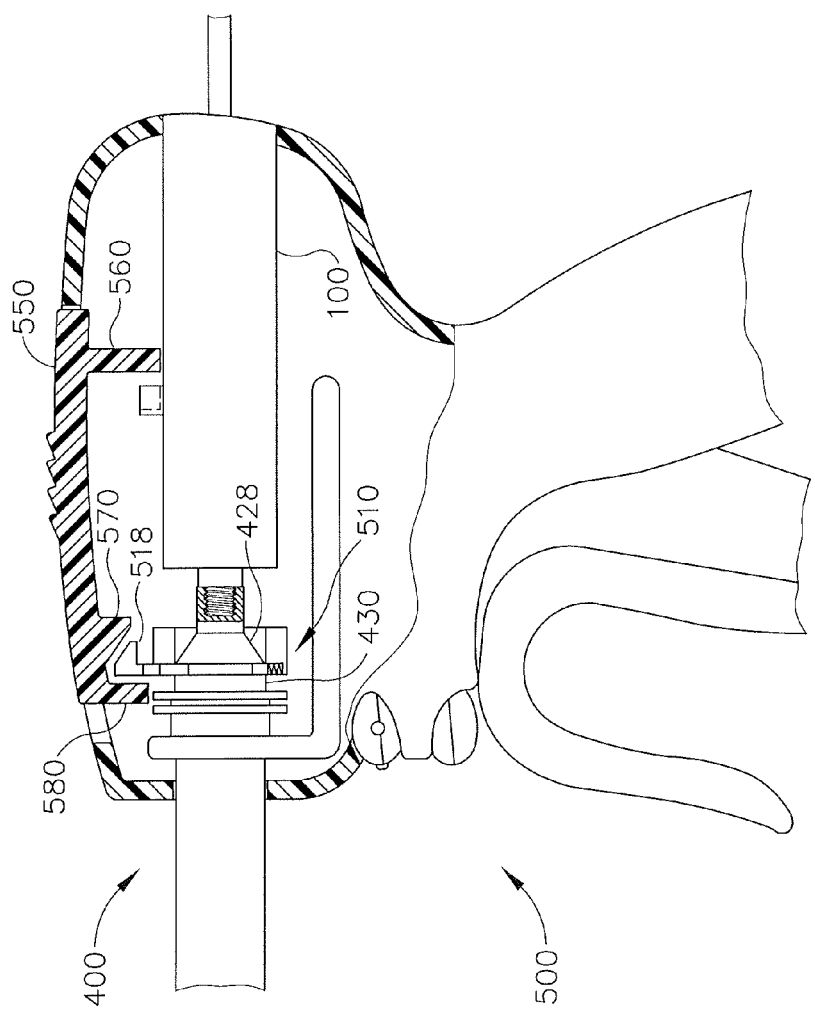
FIG. 8C depicts a partial side cross-sectional view of the assembly of FIG. 8A with the transmission assembly, the transducer, and a latching member coupled together.

FIG. 8A depicts transmission assembly (400) aligned with transmission aperture (590) of multi-piece handle assembly (500) and transducer (100) inserted within multi-piece handle assembly (500). Multi-piece handle assembly (500) of the present example is configured in a substantially similar manner to multi-piece handle assembly (60) described above, though threaded member (182) has been replaced with latching member (510). Latching member (510) of the present example is coupled to force-limiting mechanism (180) and is operable to selectively secure transmission assembly (420) to force limiting mechanism (180). As best shown in FIGS. 9A-9B, latching member (510) comprises a frame (512), a latch (514), and a pair of springs (520) disposed between a bottom surface of latch (514) and frame (512). Alternatively, resilient plastic tabs may be used instead of springs (520). In the present example frame (512) is rectangular, though it should be understood that other geometric configurations for frame (512) may be used, including circular, triangular, pentagonal, hexagonal, etc. Frame (512) includes an aperture (530) sized to permit passage of inner tubular actuating member (420) and flared portion (428) through aperture (530). Latch (514) of the present example comprises a body portion (516) and a ramped tab (518) (shown best in FIGS. 8A-8C) extending from body portion (516) outside of frame (512). As shown in FIG. 9A, when latch (514) is not depressed against springs (520), a section (532) of body portion (516) extends across a portion of aperture (530). Accordingly, when flared portion (428) of inner tubular actuating member (420) is inserted through aperture (530) and section (532) of body portion (516) extends across a part of aperture (530), then section (532) of body portion (516) is sandwiched between a distal face of flared portion (428) and outer sheath (430) to couple inner tubular actuating member (420) to latching member (510), as shown in FIG. 8C. Other configurations for latching member (510) will be apparent to one of ordinary skill in the art in view of the teachings herein. For instance, in some versions frame (512) may be a singular piece that includes a portion that extends across the longitudinal passageway for inner tubular actuating member (420) in a similar manner to latch (514). In such a version, frame (512) may be spring-loaded such that flared portion (428) of inner tubular actuating member (420) actuates frame (512) to permit passage of inner tubular actuating member (420) through an aperture. Such an aperture is formed through frame (512) and offset from the longitudinal axis of inner tubular actuating member (420) when frame (512) is not actuated.

Referring back to FIGS. 8A-8C, alternative slider (550) comprises a trigger tab (580), a transducer tab (560), and a latch ramp (570). Trigger tab (580) and transducer tab (560) of the present example are configured in a substantially similar manner as trigger tab (330) and transducer tab (310) described above. Latch ramp (570) is configured to engage and cam ramped tab (518) downwardly to open latching member (510) and permit passage of inner tubular actuating member (420) and flared portion (428) therethrough. As shown in FIG. 8B, when slider (550) is slid distally, trigger tab (580), transducer tab (560), and latch ramp (570) engage trigger yoke (170), transducer extension (130), and ramped tab (518), respectively. Accordingly, slider (550) is configured to restrict the rotational and/or longitudinal movement of transducer (100), to restrict the longitudinal movement of trigger yoke (170), and to open latching member (510) such that alternative transmission assembly (400) may be coupled to transducer (100) and latching member (510), as depicted in FIG. 8C. With slider (550) in the locked position, flared portion (428) of inner tubular actuating member (420) can pass through aperture (530). Once transmission assembly (400) of the present example is threadably coupled to transducer (100), slider (550) may be slid back to the unlocked position. This disengages trigger tab (580), latch ramp (570), and transducer tab (560). Latch (514) translates vertically in response to the resilience of springs (520) to nest section (532) of body portion (516) between flared portion (428) and outer sheath (430), thereby longitudinally coupling transmission assembly (400) to latching member (510). In some versions, slider (550) may have a return spring (not shown) to urge slider (550) toward the unlocked position. Alternatively, the return spring may be omitted and the user manually translates slider (550) between the locked and unlocked positions. In some versions that include a singular frame (512), as described above, slider (550) is configured to actuate frame (512) into the unlocked position to remove transmission assembly (400).

As with other components described herein, other suitable configurations for transmission assembly (400) and multi-piece handle assembly (500) will be apparent to one of ordinary skill in the art in view of the teachings herein.

F. Exemplary Pin Assembly

FIG. 10 shows a further exemplary alternative version for a multi-piece handle assembly (600) and transducer (700). Multi-piece handle assembly (600) of the present example may be configured in a similar manner to the multi-piece handle assemblies (60, 500) described above. In the present example, multi-piece handle assembly (600) includes actuation arm (158), trigger yoke (170), threaded member (620), and a push button (650). Push button (650) comprises a transducer pin (652), an actuator pin (654), and a trigger engagement portion (656). Trigger engagement portion (656) is configured to abut a proximal portion of trigger yoke (170) when push button (650) is depressed, thereby restricting the longitudinal movement of trigger yoke (170). Threaded member (620) is shown directly coupled to trigger yoke (170) without force-limiting mechanism (180), though it should be understood that this is merely optional. Threaded member (620) of the present example is configured to rotate freely relative to trigger yoke (170) when push button (650) is not engaged with threaded member (620). Threaded member (620) has complementary threads (622) to the threads of an inner tubular actuating member of a transmission assembly, such as external threads (228), and also includes a pin recess (624) configured to receive at least a portion of actuator pin (652). Accordingly, when actuator pin (654) is inserted into pin recess (624), the rotational movement of threaded member (620) is restricted.

Transducer (700) is configured in substantially the same way as transducer (100) described above, except transducer extension (130) is omitted. Instead of transducer extension (130), transducer (700) of the present example includes a pin recess (710) configured to receive at least a portion of transducer pin (652). Thus, when transducer pin (654) is inserted into pin recess (710), the rotational and/or translational movement of transducer (700) is restricted.

In some versions, a plurality of threaded member pin recesses (624) and/or transducer pin recesses (710) may be circumferentially disposed about threaded member (620) and/or transducer (700) such that pins (652, 654) may be inserted into any number of pin recesses (624, 710) to engage threaded member (620) and/or transducer (700). Further still, each pin recess (624, 710) may include a beveled portion such that if pins (652, 654) are not aligned with a specific pin recess (624, 710), then engagement of pins (652, 654) with beveled portions would rotate threaded member (620) and/or transducer (700) to align pins (652, 654) with one of the pin recesses (624, 710). Thus, the plurality of pin recesses (624, 710) and/or beveled portions for threaded member (620) and/or transducer (700) may facilitate engagement of pins (652, 654) with pin recesses (624, 710) in a variety of orientations and/or in situations where pins (652, 654) and pin recesses (624, 710) are misaligned.

When a user depresses push button (650), transducer pin (652) and actuator pin (654) engage transducer (700) and threaded member (620), thereby permitting the user to threadably couple a transmission assembly, such as transmission assembly (200) described above, to threaded member (620) and transducer (700). Once the user releases push button (650), one or more return springs (not shown) may return push button (650) to its original position, thereby disengaging transducer pin (652) and actuator pin (654) from their respective pin recesses (710, 624). With push button (650) released, transducer (700), threaded member (620), and the attached transmission assembly can freely rotate relative to multi-piece handle assembly (600). For instance, rotation knob (250) may be included to rotate transducer (700), threaded member (620), and the attached transmission assembly. To remove the transmission assembly, push button (650) is again depressed by the user to insert transducer pin (652) and actuator pin (654) into the respective pin recesses (710, 624) to restrict the rotational movement of transducer (700) and threaded member (620). To align the pin recess (710, 624), a mark (not shown) may be included on rotation knob (250) to indicate the circumferential location of the pin recesses (710, 624). Alternatively, a mark may be included on transducer (700). Further still, an aperture window may be provided in the casing of multi-piece handle assembly (600) to view a mark contained therein or the pin recess (624, 710) themselves. With the transmission assembly detached, the transmission assembly may be then be disposed of, cleaned for reuse, reclaimed for reprocessing and/or otherwise. In addition, multi-piece handle assembly (600) and/or transducer (700) may also be disposed of, cleaned for reuse, reclaimed for reprocessing and/or otherwise. Other suitable configurations for multi-piece handle assembly (600) and/or transducer (700) will be apparent to one of ordinary skill in the art in view of the teachings herein.

G. Exemplary Friction Assemblies

Figure 11:
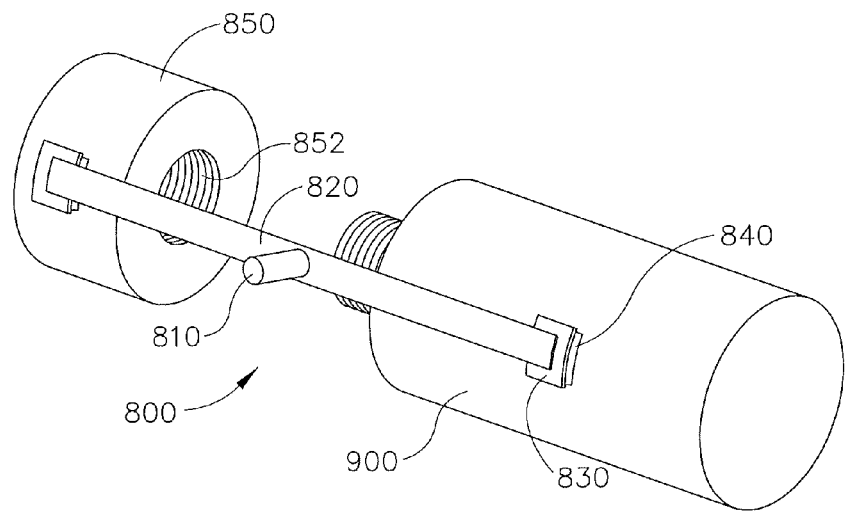
FIG. 11 depicts a perspective view of another exemplary button assembly showing a transducer and a threaded member engaged with the button assembly.
Figures 12, 13:
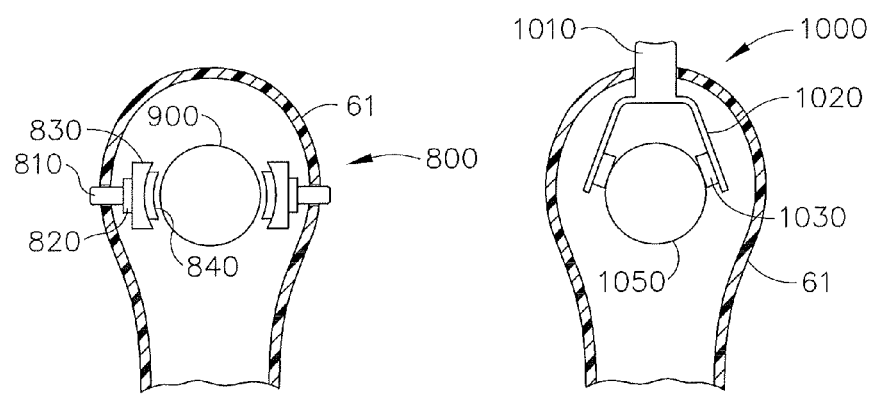
FIG. 12 depicts a rear elevation view of the button assembly of FIG. 11.
FIG. 13 depicts a rear elevation view of an exemplary alternative button assembly having a single button for an angled member with pads.

FIGS. 11-12 show still a further exemplary alternative version for a button assembly (800), a threaded member (850), and a transducer (900). In the present example, threaded member (850) is configured to rotate freely relative to a trigger yoke (not shown) when button assembly (800) is not engaged with threaded member (850). Similar to threaded members (182, 620) discussed previously, threaded member (850) includes threads (852) that complement the threads of a transmission assembly, such as external threads (228). Transducer (900) of the present example may be configured in accordance with at least some of the teachings of transducer (100) and/or transducer (700), with the omission of transducer extension (130) and/or pin recess (710), respectively.

Button assembly (800) shown in FIG. 11 comprises a button (810), a body member (820), a pair of pad mounts (830) coupled to body member (820), and a pair of pads (840) coupled to pad mounts (830). Button (810) is sized to protrude through an opening in casing (61) (partially shown in FIG. 12) such that a user may depress button (810) to engage pads (840) against transducer (900) and threaded member (850). Pad mounts (830) are a pair of arcuate members having an arc substantially conforming to the curvature of threaded member (850) and transducer (900), respectively. Pads (840) are coupled to pad mounts (830) and frictionally resist rotation of transducer (900) and/or threaded member (850) when engaged against transducer (900) and/or threaded member (850). By way of example only, pads (840) may be made from rubber (natural or synthetic), metal, plastic, carbon, ceramics, polymers, and/or any other material as will be apparent to one of ordinary skill in the art in view of the teachings herein. As shown in the example of FIG. 12, a pair of button assemblies (800) are located on opposing sides of transducer (900) and threaded member (850) such that a user can depress one or both button assemblies (800) to restrict the rotational and/or translational movement of transducer (900) and threaded member (850). With button assemblies (800) engaged with transducer (900) and threaded member (850), the user may then attach or detach a transmission assembly, such as transmission assembly (200 or 400). While a pair of button assemblies (800) are shown, it should be understood that a single button assembly may be used. In addition, if more than one button assembly (800) is used, button assemblies (800) need not be limited to opposing placement about transducer (900) and threaded member (850). Indeed, button assemblies (800) may be adjacent to one another or in any other suitable location relative to the other. Still other configurations for button assembly (800), threaded member (850), and/or transducer (900) will be apparent to one of ordinary skill in the art in view of the teachings herein.

FIG. 13 shows an alternative button assembly (1000) that comprises a button (1010), an angled member (1020), and a pair of pads (1030) coupled to angled member (1020). Button (1010) is sized to protrude through an opening in casing (61) (partially shown in FIG. 13) such that a user may depress button (1010) to engage pads (1030) against a transducer (1050) and/or a threaded member (not shown). Angled member (1020) includes a central portion and a pair of angled portions extending from the central portion such that the angled portions form a V shape. In the example shown, the angled portions are at an angle relative to each other so that when angled member (1020) is actuated downwardly by button (1010), pads (1030) on the angled portions of angled member (1020) engage the surface of transducer (1050) and/or the threaded member. Of course angled member (1020) may have other configurations, including a C-shape, a flat plate, and or any other configuration as will be apparent to one of ordinary skill in the art in view of the teachings herein. Pads (1030) are coupled to angled member (1020) and frictionally resist rotation of transducer (1050) and/or the threaded member when engaged against transducer (1050) and/or threaded member. By way of example only, pads (1030) may be made from rubber (natural or synthetic), metal, plastic, carbon, ceramics, polymers, and/or any other material as will be apparent to one of ordinary skill in the art in view of the teachings herein. In the example shown, a single button assembly (1000) is included to frictionally engage transducer (1050), but it should be understood that more than one button assemblies (1000) may be used to restrict the rotational and/or translational movement of transducer (1050) and/or the threaded member. With button assembly (1000) engaged with transducer (1050), the user may then attach or detach a transmission assembly, such as transmission assembly (200 or 400). Still other configurations for button assembly (1000) will be apparent to one of ordinary skill in the art in view of the teachings herein.

While the various foregoing versions include sliders and/or buttons that can be actuated by a user to prevent rotation of the transducers and/or threaded members, it should be understood that trigger (68) may alternatively be mechanically linked to the buttons and/or sliders to prevent such rotation when trigger (68) is in the open position. By way of example only, a member may extend proximally from trigger yoke (170) and include an actuator tab and a transducer tab extending downwardly in a similar manner to actuator tab (320) and transducer tab (310). When trigger (68) is in the open position, the actuator tab and the transducer tab engage engagement portion (186) of threaded member (182) and engagement region (136) of transducer (100), respectively. Thus, with trigger (68) in the open position, a transmission assembly may be coupled to or decoupled from threaded member (182) and transducer (100). When trigger (68) is actuated to the closed position, the member translates distally to disengage the actuator tab and the transducer tab, thereby permitting free rotation of threaded member (182) and transducer (100).

In some versions, trigger (68) may include a third pivot position in which trigger (68) may be pulled distally past the open position described previously. This third position engages the actuator tab and the transducer tab, described above, with engagement portion (186) of threaded member (182) and engagement region (136) of transducer (100), respectively. Thus, with trigger (68) pulled forward, a transmission assembly may be coupled to or decoupled from threaded member (182) and transducer (100). Including such a third pivot position would permit rotation of the transmission assembly when trigger (68) is in the second position and clamp arm (84) is open. Still further configurations for surgical instrument (50) will be apparent to one of ordinary skill in the art in view of the teachings herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) an acoustic transmission assembly comprising:
      (i) a waveguide having a proximal end and a distal end, and
      (ii) an end effector, wherein the end effector comprises a clamp arm and an ultrasonic blade, wherein the clamp arm is movable relative to the ultrasonic blade between an open position and a closed position, wherein the ultrasonic blade is coupled to the distal end of the waveguide;
   (b) a transducer; and
   (c) a body, wherein the body is configured to receive a portion of the acoustic transmission assembly, wherein the body comprises:
      (i) a locking mechanism, wherein the locking mechanism comprises a movable locking member, wherein the locking mechanism is operable to selectively restrict rotational movement of the transducer relative to the body, and
      (ii) a clamp arm actuating member operable to move the clamp arm between the open position and the closed position,
   wherein the locking member is movable independently relative to the clamp arm actuating member or the clamp arm;
   wherein the locking mechanism is further operable to lock the clamp arm actuating member in a first position.

2. The surgical instrument of claim 1 wherein the acoustic transmission assembly further comprises an inner tubular actuating member coaxially disposed about the waveguide and having a proximal end, wherein the inner tubular actuating member couples the clamp arm actuating member with the clamp arm.

3. The surgical instrument of claim 2 further comprising an actuator coupling member coupled with the clamp arm actuating member, wherein the actuator coupling member is operable to selectively couple to a proximal end of the inner tubular actuating member.

4. The surgical instrument of claim 3 wherein the actuator coupling member comprises threads, and wherein the proximal end of the inner tubular actuating member comprises threads that are complementary to the threads of the actuator coupling member.

5. The surgical instrument of claim 2 further comprising an actuator coupling member coupled with the clamp arm actuating member, wherein the actuator coupling member comprises a latching mechanism, wherein the proximal end of the inner tubular actuating member comprises a flared portion and wherein the latching mechanism is configured to selectively restrict longitudinal movement of the inner actuating member relative to the body when the latching mechanism is engaged with the flared portion.

6. The surgical instrument of claim 5 wherein the locking mechanism comprises a slider having a transducer tab and a ramp, wherein the latching mechanism comprises a release tab, wherein the transducer comprises a transducer engagement region, and wherein the ramp is configured to engage the release tab to unlatch the latching mechanism and the tab is configured to engage the transducer engagement region to selectively restrict rotational movement of the transducer relative to the body when the slider is actuated from a first position to a second position.

7. The surgical instrument of claim 2 wherein the acoustic transmission assembly further comprises a rotation knob, wherein the rotation knob is configured to rotate the inner tubular actuating member and the waveguide relative to the body.

8. The surgical instrument of claim 7 wherein the rotation knob comprises a connector that couples to the body when the proximal end of the acoustic transmission assembly is coupled with the body.

9. The surgical instrument of claim 1 further comprising an actuator coupling member coupled with the clamp arm actuating member, wherein the locking mechanism comprises a slider having a plurality of tabs, wherein the transducer comprises a transducer engagement region, wherein the actuator coupling member comprises an actuator engagement region, and wherein the plurality of tabs are operable to engage the transducer engagement region and the actuator engagement region to selectively restrict rotational movement of the actuator coupling member and rotational movement of the transducer when the slider is actuated from a first position to a second position.

10. The surgical instrument of claim 1 wherein the clamp arm actuating member comprises a trigger, wherein the trigger is pivotable between a first position and a second position, wherein the first position is operable to engage the locking mechanism to selectively restrict rotational movement of the transducer relative to the body.

11. The surgical instrument of claim 1 wherein the clamp arm actuating member comprises a trigger, wherein the trigger is proximally pivotable between a first and a second position, and wherein the trigger is distally pivotable between the first position and a third position, wherein the third position is operable to engage the locking mechanism to selectively restrict rotational movement of the transducer relative to the body.

12. The surgical instrument of claim 1 wherein the body further comprises a transducer aperture configured to receive a portion of the transducer, wherein a portion of the transducer is insertable into the transducer aperture.

13. The surgical instrument of claim 1 wherein the proximal end of the waveguide is operable to selectively couple to the transducer.

14. The surgical instrument of claim 1 wherein the locking mechanism is further operable to lock the clamp arm in the open position while simultaneously restricting rotational movement of the transducer relative to the body.

15. A surgical instrument comprising:
(a) an ultrasonic transducer;
(b) a shaft assembly, wherein the shaft assembly comprises an ultrasonic waveguide, wherein the ultrasonic waveguide is configured to couple with the ultrasonic transducer;
(c) an end effector at a distal end of the shaft assembly, wherein the end effector comprises an ultrasonic blade, wherein the ultrasonic blade is configured to couple with the ultrasonic waveguide; and
(d) a body, wherein the shaft assembly extends distally from the body, wherein at least a portion of the shaft assembly is rotatable relative to the body, wherein the body includes a slidable locking feature, wherein the slidable locking feature is slidable between a first position and a second position, wherein the slidable locking feature is configured to permit rotation of the ultrasonic transducer relative to the body when the slidable locking feature is in the first position, wherein the slidable locking feature is configured to prevent rotation of the ultrasonic transducer relative to the body when the slidable locking feature is in the second position;
wherein the body further comprises a trigger pivotable between a first position and a second position to selectively actuate the end effector;
wherein the shaft assembly defines a longitudinal axis, wherein the slidable locking feature is slidable along a path that is parallel to the longitudinal axis;
wherein the slidable locking feature is further configured to prevent the trigger from pivoting from the first position to the second position when the slidable locking feature is in the second position.

16. The surgical instrument of claim 15 wherein the end effector further comprises a clamp arm movable toward and away from the ultrasonic blade, wherein the body further comprises a trigger pivotable between a first position and a second position to selectively move the clamp arm toward the ultrasonic blade.

17. A surgical instrument comprising:
(a) an acoustic transmission assembly comprising:
(i) a waveguide having a proximal end and a distal end, and
(ii) an end effector, wherein the end effector comprises a clamp arm and an ultrasonic blade, wherein the clamp arm is movable relative to the ultrasonic blade between an open position and a closed position, wherein the ultrasonic blade is coupled to the distal end of the waveguide;
(b) a transducer; and
(c) a body, wherein the body is configured to receive a portion of the acoustic transmission assembly, wherein the body comprises:
(i) a locking mechanism, wherein the locking mechanism comprises a movable locking member, wherein the locking mechanism is operable to selectively restrict rotational movement of the transducer relative to the body, and
(ii) a clamp arm actuating member operable to move the clamp arm between the open position and the closed position,
wherein the locking member is movable independently relative to the clamp arm actuating member or the clamp arm;
wherein the clamp arm actuating member comprises a trigger, wherein the trigger is pivotable between a first position and a second position, wherein the first position is operable to engage the locking mechanism to selectively restrict rotational movement of the transducer relative to the body.

* * * * *